(12) United States Patent
Calt, Jr. et al.

(10) Patent No.: US 8,574,870 B1
(45) Date of Patent: Nov. 5, 2013

(54) PROCESS OF MANAGED ECOSYSTEM FERMENTATION

(71) Applicant: Integrated BioChem, LLC, Raleigh, NC (US)

(72) Inventors: Edward Arthur Calt, Jr., Raleigh, NC (US); Herbert Graham Tull, IV, Cary, NC (US); Stanley Sylvester Toporek, Raleigh, NC (US)

(73) Assignee: Integrated BioChem, LLC, Raleigh, NC (US)

( * ) Notice: Subject to any disclaimer, the term of this patent is extended or adjusted under 35 U.S.C. 154(b) by 0 days.

(21) Appl. No.: 13/737,264

(22) Filed: Jan. 9, 2013

Related U.S. Application Data

(62) Division of application No. 13/493,119, filed on Jun. 11, 2012, now Pat. No. 8,367,372.

(51) Int. Cl.
*C12P 1/00* (2006.01)

(52) U.S. Cl.
USPC .............................. 435/41; 435/141; 429/408

(58) Field of Classification Search
USPC ..................................... 435/41, 141; 429/408
See application file for complete search history.

(56) References Cited

U.S. PATENT DOCUMENTS

| 5,431,819 | A | * | 7/1995 | Hack et al. | 210/603 |
| 2002/0038058 | A1 | | 3/2002 | Holtzapple et al. | |
| 2008/0193994 | A1 | | 8/2008 | Choate et al. | |
| 2008/0311640 | A1 | | 12/2008 | Cox et al. | |
| 2011/0111475 | A1 | | 5/2011 | Kuhry et al. | |

FOREIGN PATENT DOCUMENTS

| EP | 1902139 B1 | 1/2011 |
| WO | 2010109203 A1 | 9/2010 |
| WO | 2012170989 A1 | 12/2012 |

OTHER PUBLICATIONS

Esdale, W.J. Manipulation of Ruminal Fermentation: Effect of Altering Ruminal pH on Volatile Fatty Acid Production. Journal of Diary Science. 1971. vol. 55(7). pp. 964-970.*
International Search Report and Written Opinion mailed Jan. 28, 2013, (ISA:KIPO), for related application PCT/US2012/041852 filed Jun. 11, 2012 and published Dec. 13, 2012, as WO 2012/170989.

* cited by examiner

*Primary Examiner* — Susan Hanley
*Assistant Examiner* — Nghi Nguyen
(74) *Attorney, Agent, or Firm* — NK Patent Law, PLLC

(57) ABSTRACT

The presently disclosed subject matter relates to Managed Ecosystem Fermentation (MEF) which is a continuous microbial process utilizing a managed ecosystem approach employing dozens to thousands of species of microorganisms, occurring in a controlled artificial environment and consuming organic materials without benefit of sterilization. The process of utilizing this fermentation for the consumption of organic materials on a continuous basis is within the scope of this disclosed subject matter. The process of separating chemicals as industrial chemicals from this fermentation on a continuous basis is within the scope of this disclosed subject matter. The process of separating biomass useful as high protein animal feed or fertilizer from this fermentation on a continuous (or semi-continuous) basis is within the scope of this disclosed subject matter.

32 Claims, 18 Drawing Sheets

US 8,574,870 B1

PROCESS OF MANAGED ECOSYSTEM FERMENTATION

CROSS-REFERENCE TO RELATED APPLICATIONS

This application is a divisional of U.S. Non-provisional patent application Ser. No. 13/493,119, filed Jun. 11, 2012, now U.S. Pat. No. 8,367,372, and claims priority to U.S. Provisional Patent Application No. 61/495,183, filed Jun. 9, 2011, the disclosure of which is hereby incorporated by reference in its entirety. This application is related to International Patent Application No. PCT/US2012/041852 filed Jun. 11, 2012.

TECHNICAL FIELD

The presently disclosed subject matter relates to a process for managed ecosystem fermentation (MEF) of organic feedstocks to produce industrial chemical and biomass products.

BACKGROUND

Microbial ecosystems are found naturally in many places, including the digestive tracts of most animals. The starting point of this process is the microbial fauna found in the rumen organ of cattle and other ruminant animals. These natural microbial ecosystems are continuous processes and do not require sterilized feedstocks. However, natural microbial ecosystems found in animals are size limited by the host organism, are not actively managed to modulate the output materials, and cannot support extracting large volumes of chemicals or biomass for industrial purposes without detriment to the host animal.

Microbial ecosystems are also found in artificial environments, such as anaerobic digesters and activated sludge type waste water treatment plants. These installations can scale to large sizes but do not actively manage the mix of species within their microbial ecosystems, nor do they recover both chemicals and biomass for use in industrial products.

Accordingly, a need for replicating microbial ecosystems exists that addresses these and other issues associated with the prior art.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment of the presently disclosed subject matter, a method is provided for generating resources from feedstocks, the method comprising fermenting an organic feedstock with a rumen to generate a resource. The organic feedstock comprises one or more of catering waste, biodiesel waste, agricultural waste, food processing plant waste, wood pulp, paper mill sludge, cotton gin waste, sewage sludge, slaughter house waste, organic fraction of municipal solid waste (OFMSW), or algae. The rumen comprises a rumen from a ruminant animal. The resources generated comprise one or more of chemicals, volatile fatty acids, long chain fatty acids, lipids, high protein animal feed, fertilizer, amino acids, enzymes, ethanol, butanol, biogas, or water.

In one embodiment of the method, the resource comprises chemicals and the method comprises shunting at least a portion of the chemicals to a biogas generator, wherein the biogas generator is a second fermenter that comprises the rumen; and fermenting the chemicals and the rumen in the biogas generator to generate biogas.

In one embodiment, the method comprises utilizing at least a portion of the generated resource chemicals, the generated resource hydrogen, and/or the generated resource biogas to generate power and/or heat for the method.

In one embodiment, the method comprises reclaiming at least a portion of the generated resource water.

In one embodiment, the method comprises adding one or more of a microorganism, a bacteria, a butyric acid producing bacteria, a cellulosic bacteria, a yeast, a fungi, a protozoa, earth worm microbes, termite microbes, or cecum microbes.

In one embodiment of the presently disclosed subject matter, a system is provided for generating resources from organic feedstocks, the system comprising a grinder/mixer configured to receive an organic feedstock and a rumen, and a fermenter configured to receive the organic feedstock and the rumen and configured to ferment the organic feedstock to generate a resource. The resources generated comprise one or more of chemicals, volatile fatty acids, long chain fatty acids, lipids, high protein animal feed, fertilizer, amino acids, enzymes, ethanol, butanol, biogas, or water.

In one embodiment of the system, the fermenter is configured to fractionate the generated resource lipids, chemicals, biogas, and biomass; and the system comprises a lipid separation unit configured to generate a lipid product; a chemical separation unit configured to generate a chemical product; a biomass separation unit configured to generate a biomass product; and a biogas generator configured to generate biogas from at least a portion of the generated resource chemicals.

In one embodiment, the chemical product comprises one or more of an acetic acid, a proprionic acid, an isobutyric acid, a butyric acid, an isovaleric acid, a valeric acid, a lactic acid, or a hexanoic acid.

In one embodiment, the biomass product is selected from the group consisting of a fertilizer, a high protein animal feed, and a soil enhancer having live microbes.

In one embodiment, the feedstock comprises algae and the lipid product is the lipid from the algae.

In one embodiment, the system comprises a power generation and heat recovery unit configured to generate power and/or heat, wherein the generated power and/or heat are utilized in the system.

In one embodiment, the system comprises a remote facility configured to monitor and/or control the fermenter through use of a communications link between the remote facility and the fermenter.

DETAILED DESCRIPTION

The presently disclosed subject matter provides methods for generating resources from feedstocks. More specifically, the methods provided herein comprise fermenting an organic feedstock with a rumen to generate a resource including one or more of chemicals, biomass, lipids, and biogas. The fermenting of an organic feedstock with a rumen from a ruminant animal is herein referred to as Managed Ecosystem Fermentation ("MEF") and is based on naturally occurring colonies of microbes with thousands of different species forming a symbiotic whole. A natural microbial ecosystem is internally symbiotic, as the many species are dependent upon each other and cannot be independently cultured. MEF uses natural microbial ecosystems as a building block to develop complex industrial processes. MEF installations use the metabolites (otherwise referred to herein as "chemicals") and microbial mass produced by the microbes, and the residuals from the feedstocks as recovered products.

Figure 1:
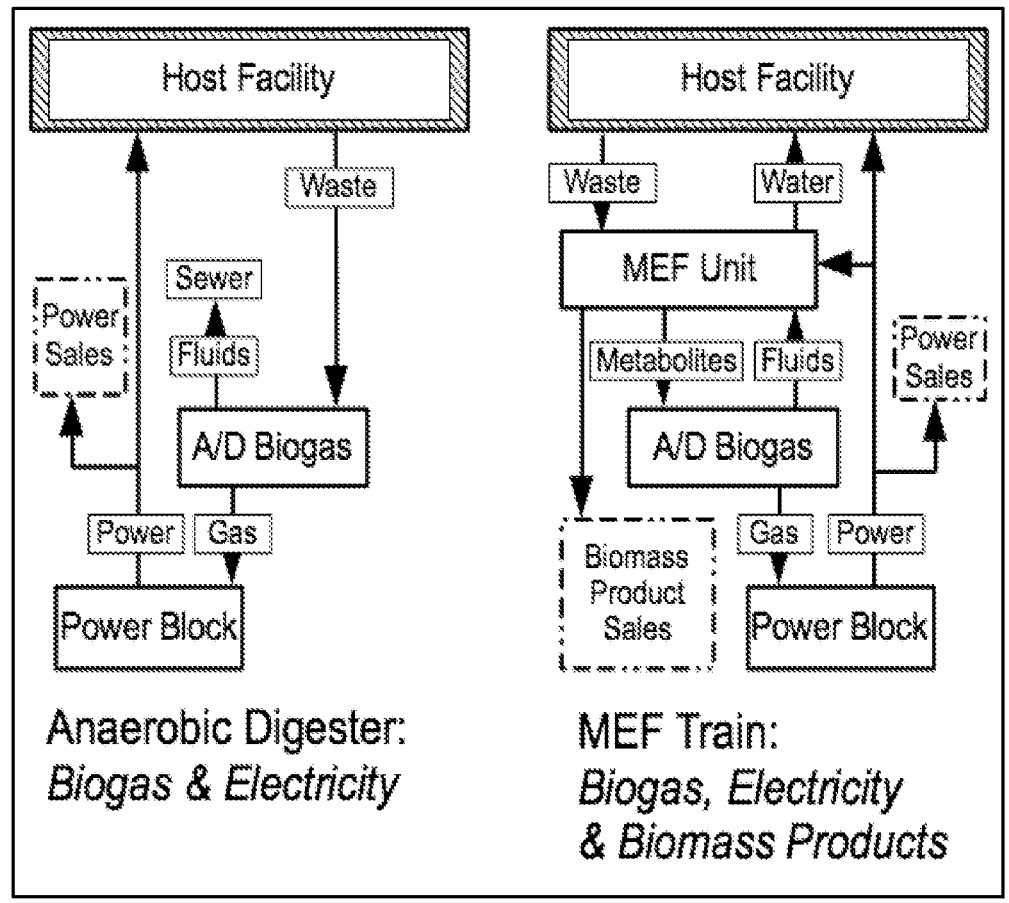
FIG. 1 shows a comparison of a traditional anaerobic digester and a Managed Ecosystem Fermentation (MEF) train for generating resources including metabolites, biomass products, biogas, and electricity from fermentation of waste feedstocks.
Figure 2:
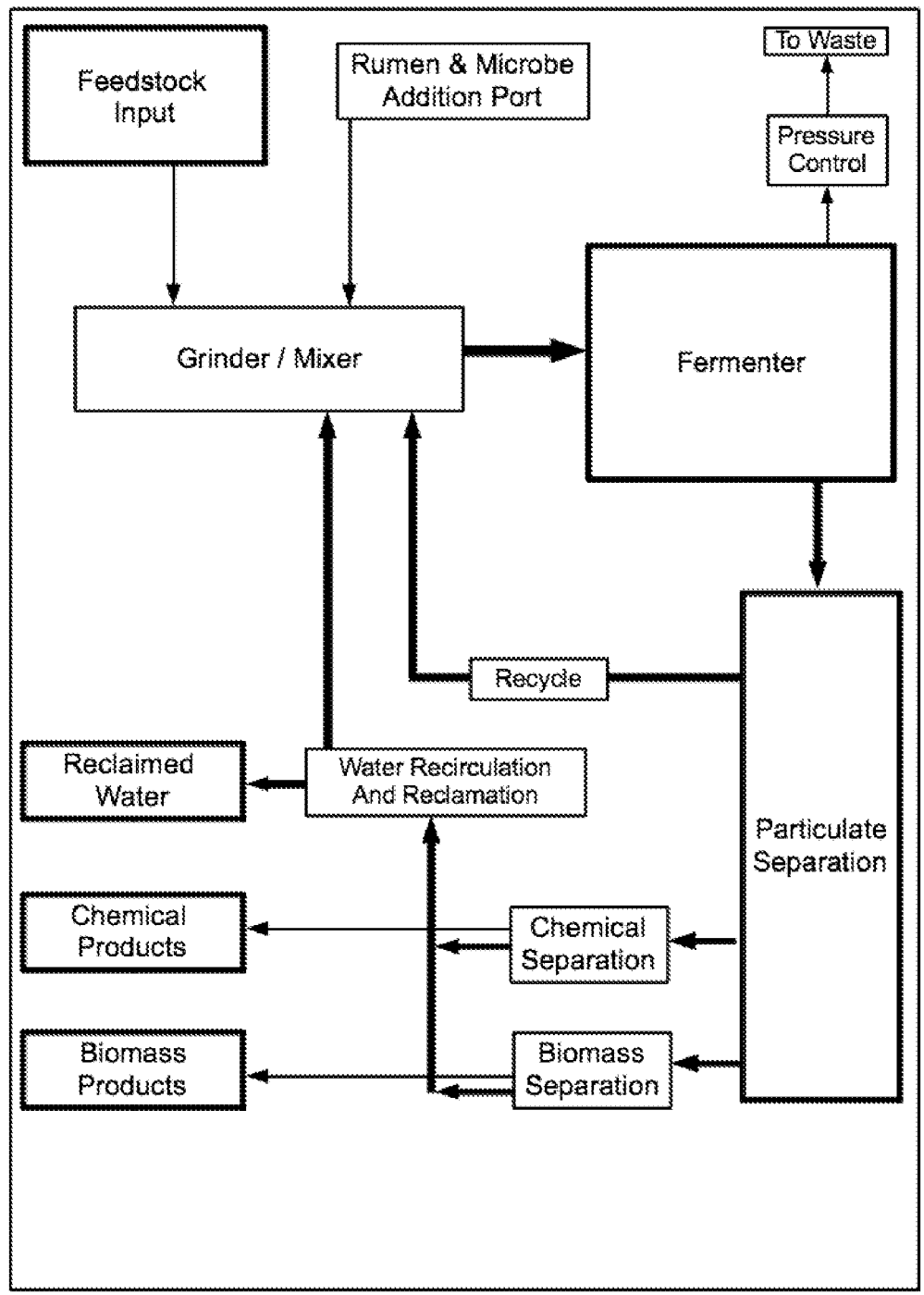
FIG. 2 is a flow diagram illustrating a Managed Ecosystem Fermentation (MEF) train for generating resources including chemical products, biomass products, biogas, power and heat, and reclaimed water from fermentation of organic feedstocks with rumen. The MEF train allows for stirring or agitation of the fermenter and separation of the chemicals and biomass in a particulate separation unit.

The conceptual differences between MEF and other natural or industrial microbial processes is the degree of management control applied and the number of products harvested. MEF is between the two extremes of unmanaged microbial fermentations in anaerobic digesters (AD) and the single species fermentations of the pharmaceutical industry. MEF takes a role in actively managing and controlling the microbial colony: adding species that produce desired products, but avoids the DNA manipulations used in genetic engineering. An example of a schematic diagram of an MEF is illustrated in FIG. 2.

Management of many natural microbial species rather than trying to add features to a single microbe has several major advantages. The microbial species in a naturally occurring microbial ecosystem already have their own niche in nature and many cannot be cultured outside their ecosystem. These are not new microbes, so they pose a low risk of becoming new pathogens. Because all the species in a MEF function holistically, the need to protect any one microbe or process from the "outside world" by sterilizing all equipment and feedstock is a large cost that is avoided. The diversity of microbes forms a self-defensive mechanism to ensure survival of the microbial consortium. MEF processes can screen potential mixtures of microbial ecosystems and their product yields at a faster rate than scientists can modify the genetics of a single species and test their results. MEF focuses on selecting and combining many naturally occurring species into stable ecosystems with additional properties beyond those of the original ecosystem.

The characteristics of MEF offer several technical advantages as an industrial process. For example, MEF occurs at moderate temperatures and near atmospheric pressures, so construction costs can be lower than processes with much higher temperatures and pressures, such as pyrolysis.

Rumen produces few toxic materials, as evidenced by long natural lifespans of many ruminants, indicating there should be little risk of new toxins entering the environment from rumen based MEF processes. Additionally, a strong QA/QC program will test and verify product safety on an ongoing basis. In contrast, literature points to the ability of rumen microbes to detoxify some environmental toxins, including aflatoxin.

MEF is an anaerobic process operating near neutral pH values, so the liability risk from a spill is limited. Oxygen in the air will quickly halt the process and the fluid is only mildly corrosive at pH 5 to 6.5. All of the microbes are naturally occurring, many are soil bacteria, and unlikely to harm plants or groundwater.

MEF is robust; ruminant animals can live 20 years without a microbial failure. This robustness of MEF means lower maintenance expenses in caring for the microbes.

MEF is adaptable to different feedstocks. The minimum transition time from grass to grain for cattle is several days. Microbes from cattle rumen also adapt to a wide variety of feedstocks in the lab. This adaptability eliminates the need for strain archiving as used in pharmaceuticals.

MEF can be modified by adding additional microbes to the ecosystem. Research with Australian sheep has demonstrated that the ability to digest specific tannins can be acquired by animals receiving additional rumen microbes.

MEF does not require a sterilized feedstock. This property avoids a process that could be very difficult and expensive for high volume feedstocks.

The methods and compositions of the presently disclosed subject matter are described in greater detail herein below.

DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims. Thus, for example, reference to "a chemical" or reference to "a lipid" includes a plurality of such chemicals or such lipids, and so forth.

The term "metabolite" is herein used interchangeably, for the purposes of the specification, drawings, and claims, with the term "chemical".

As used herein, the blocks illustrated in FIGS. 2-12 are sometimes referred to herein as "units" and are meant to represent blocks of equipment that can contain multiple elements to perform the various tasks.

As used herein, the term "feedstock" means the organic materials placed into the MEF process for conversion to output materials (or otherwise referred to herein as "resources"). The term "organic feedstock" is used herein for the purposes of the specification, drawings, and claims to refer to any feedstock of an organic nature. The term "organic" as it is used herein for the purposes of the specification, drawings, and claims, is meant to be understood in its broadest sense as being of, relating to, or derived from living matter. Accordingly, the organic feedstock of the presently disclosed subject matter can comprise, for example, but is not limited to one or more of catering waste, biodiesel waste, agricultural waste, food processing plant waste, wood pulp, shredded paper, paper mill sludge, cotton gin waste, sewage sludge, slaughter house waste, organic fraction of municipal solid waste (OFMSW), or algae, or combinations thereof. "Feed grade" organic feedstock for the purposes of the specification, drawings, and claims means organic material that is approved for feeding to livestock. In some cases it may be abbreviated as ("FG") in this document. "Adulterated" organic feedstock means for purposes of the specification, drawings, and claims any organic material that is not approved for feeding to livestock. Most organic wastes will be considered adulterated and therefore the MEF products from these sources will not be acceptable as animal feed.

The term "rumen" is used herein for the purposes of the specification, drawings, and claims to refer to one or more of a rumen from a ruminant animal. Specific examples of the rumen include, for example, but are not limited to one or more of a bovine rumen, a sheep rumen, a goat rumen, a deer rumen, or a bison rumen, or combinations thereof. In addition to the rumen, one or more microorganisms can be added to the MEF of the presently disclosed subject matter. The term "microorganism" is herein used interchangeably with the term "microbe" and means for the purposes of the specification, drawings, and claims, any microscopic organism. Examples of microorganisms include, but are not limited to, bacteria, butyric acid producing bacteria including, for example, *Clostridium acetobutylicum, Clostridium butyricum, Clostridium kluyveri, Clostridium pasteurianum, Fusobacterium nucleatum, Butyrivibrio fibrisolvens, Eubacterium limosum,* cellulosic bacteria, earth worm microbes, termite microbes, cecum microbes, rabbit cecum microbes, horse cecum microbes, yeast, industrial yeast, brewer's yeast, fungi, *Trichoderma reesei*, and protozoa, and combinations thereof. By "cellulosic bacteria" is meant bacteria capable of breaking down cellulose, for example, by hydrolysis. Cellulosic bacteria include bacteria in the rumen or bacteria in the intestine of certain non-rumen species that are capable of digesting cellulose to volatile fatty acids including acetic, butyric, and propionic. By earth worm microbes or termite microbes is meant the microbes in the gut of the earth worm or termite that are capable of breaking down cellulose. By cecum microbes is meant the microbes in the cecum of an animal that are capable of breaking down cellulose. By *Trichoderma reesei* is meant a fungus having the capacity to secrete large amounts of cellulolytic enzymes such as, for example, cellulases and hemicellulases.

The term "resource" is used herein for the purposes of the specification, drawings, and claims to refer to one or more of chemicals, lipids, volatile fatty acids ("VFAs"), long chain fatty acids, acetic acid, proprionic acid, isobutyric acid, butyric acid, isovaleric acid, valeric acid, lactic acid, hexanoic acid, ethanol, butanol, biomass, high protein animal feed, fertilizer, phosphate fertilizer, nitrogen fertilizer, proteins, amino acids, lysine, enzymes, cellulase, alpha-amylase, histidase, lysozyme, penicillin acylase, biogas, methane, hydrogen, carbon dioxide, and water.

The term "chemical" is meant to be interpreted in its broadest sense for the purposes of the specification, drawings, and claims, as anything made of matter that is present in the MEF of the presently disclosed subject matter. In one sense, the term "chemical" is used herein to mean any chemical, biochemical, or metabolite that can be produced by a ruminant animal, produced by a microorganism that is capable of breaking down cellulose, or produced by a MEF. Specific examples of chemicals include, but are not limited to, volatile fatty acids, long chain fatty acids, acetic acid, proprionic acid, isobutyric acid, butyric acid, isovaleric acid, valeric acid, lactic acid, hexanoic acid, ethanol, and butanol.

The term "biomass" and the term "microbial biomass" and the term "biomass product" and the term "biomass materials" are herein used interchangeably, for the purposes of the specification, drawings, and claims. "Biomass product" means for the purposes of the specification, drawings, and claims, the output stream of the MEF process containing the majority of the biomass in the form of cells, cellular debris, proteins, enzymes, or amino acids. These biomass materials can be removed from the system in the raw state or processed further to make additional biomass products.

The term "protein" means, as it is used herein for the purposes of the specification, drawings, and claims, any amino acid, peptide, enzyme, or protein molecule and the term "protein" is herein used interchangeably with the term "polypeptide" the term "peptide" the term "amino acid" the term "enzyme" and a term for any specific amino acid or any specific enzyme.

To assess how and what the MEF will produce, follow the flow of carbon from feedstock to product. The carbon balance shown in Table 1 has two parts because two stages of fermentation are used. Stage one is the initial fermentation and modeled on the rumen fermentation of cattle because that is the original source of the microbial ecosystem. Stage two is a biogas generator consuming the VFAs from stage one and is modeled on commercial biogas generators, since it uses the same methanogenic microbes. The carbon balance includes only the digestible fraction of the feedstock. Indigestibles, such as lignin, are not part of the yield, but will appear as compost material at the exit of the process. The summarized values in Table 2 are the overall carbon allocations across both processes.

TABLE 1

Carbon Partitioning
Carbon Partitions in each stage of fermentation occurring in MEF.

| Stage 1 Process: Acidogenesis | Stage 1 Percent | Stage 2 Process: Methanogenesis | Stage 2 Percent | Composite Carbon Partition Stage 1 + 2 = Total | Total Percent |
|---|---|---|---|---|---|
| Chemicals; VFA | 56.0% | VFA → $CH_4$ | 60.0% | Chemical, VFA → $CH_4$ | 33.6% |
|  |  | VFA → $CO_2$ | 40.0% | Chemical, VFA → $CO_2$ | 22.4% |
| Biomass; Microbes | 25.0% |  |  | Biomass; Microbes | 25.0% |
| Fermentation gas ($CO_2$) | 18.5% |  |  | Fermentation gas ($CO_2$) | 18.5% |
| Fermentation gas ($CH_4$) | 0.5% |  |  | Fermentation gas ($CH_4$) | 0.5% |
| Totals: | 100.0% | Totals: | 100.0% | Totals: | 100.0% |

TABLE 2

Digested Carbon Summary
Summary of carbon partition

| Carbon Allocation | Percent |
|---|---|
| Methane | 34% |
| Carbon Dioxide | 41% |
| Microbial Carbon | 25% |
| Total: | 100% |

The yields of methane and biomass are the sources of income, with biomass having far more value than methane. In one embodiment, the methane is converted to electric power and process heat as part of the process. The yield of methane appears adequate to provide enough heat and power to drive the overall process.

The biomass is a composite of cells, enzymes, proteins, and amino acids. While this material can be harvested dried and used in bulk as fertilizer or a high protein animal feed (HPAF), there is significant potential income in separating enzymes and amino acids for sale separately. MEF as an industrial process is more complex than a biogas unit, but the HPAF and other bio-products sell for much more than the methane or electricity.

Managed Ecosystem Fermentation (MEF) systems, processes, and methods for implementing thereof are disclosed herein (see FIGS. 2-12). The MEF has several important characteristics. The microbial fermentations exist symbiotically within a controlled mechanical environment. The microbial ecosystem is symbiotic between the many species within the fermentation and also the entire ecosystem is symbiotically dependent on the external mechanical environment in which it is located. Manipulation of the external environment is one of the management tools used in MEF processes.

The Managed Ecosystem Fermentation (MEF) system of the presently disclosed subject matter does not require sterilized feedstocks. The diversity of species within the ecosystem appear to offer protection to the entire ecosystem. No animal sterilizes everything it eats; the digestive microbial ecosystem appears to protect it. The MEF processes described herein utilize the diversity of microbial species as a protective mechanism, so sterilization of the feedstock is not required.

Ecosystem fermentations can consume a wide variety of organic materials, and provide a stable output for years at a time. The behavior of rumen in cattle fed on pasture or fed on grain is different; however, a transition time is required between the two feeding programs. The human diet demonstrates this diversity of inputs and long term stability. Controlling of the feedstock input characteristics can manipulate the output materials from the MEF system, providing another management tool used in MEF processes.

MEF processes can be adapted to new tasks by manipulating which microbial species are present in the ecosystem. Hybridizing the microbial ecosystem by controlling which specific species are included in the managed ecosystem is another tool for operating MEF installations.

Ecosystem processes can produce a wide variety of chemicals and biomass species simultaneously. MEF processes can extract the chemicals and biomass produced; together or separately, as solids, liquids or gases. The chemicals and biomass materials can be further separated into chemical families or individual compounds.

In one embodiment, the presently disclosed subject matter provides a method for generating resources from feedstocks, the method comprising fermenting an organic feedstock with a rumen to generate a resource.

For the MEF methods and systems of the presently disclosed subject matter, the organic feedstock can include, for example, but is not limited to catering waste, biodiesel waste, agricultural waste, food processing plant waste, wood pulp, shredded paper, paper mill sludge, cotton gin waste, sewage sludge, slaughter house waste, organic fraction of municipal solid waste (OFMSW), or algae, or combinations thereof.

For the MEF methods and systems of the presently disclosed subject matter, the rumen is one or more of a rumen from a ruminant animal, and specific examples include, but are not limited to a bovine rumen, a sheep rumen, a goat rumen, a deer rumen, or a bison rumen, or combinations thereof.

The resources generated in the MEF methods and systems of the presently disclosed subject matter are one or more of chemicals, lipids, volatile fatty acids, long chain fatty acids, acetic acid, proprionic acid, isobutyric acid, butyric acid, isovaleric acid, valeric acid, lactic acid, hexanoic acid, biomass, high protein animal feed, fertilizer, phosphate fertilizer, nitrogen fertilizer, proteins, amino acids, lysine, enzymes, cellulase, alpha-amylase, histidase, lysozyme, penicillin acylase, ethanol, butanol, biogas, methane, hydrogen, carbon dioxide, and water.

One embodiment of the method is depicted in the flow diagram illustrated in FIG. 2. FIG. 2 shows a Managed Ecosystem Fermentation (MEF) train for generating resources including chemical products, biomass products, and reclaimed water from fermentation of the organic feedstock with the rumen. In this embodiment, the method comprises stirring and/or agitating the organic feedstock during the fermenting and separating the chemicals in the fermentation liquid from the particulate biomass using one or more filters, or other separation technologies, which is depicted in FIG. 2 as "Particulate Separation."

Figure 3:
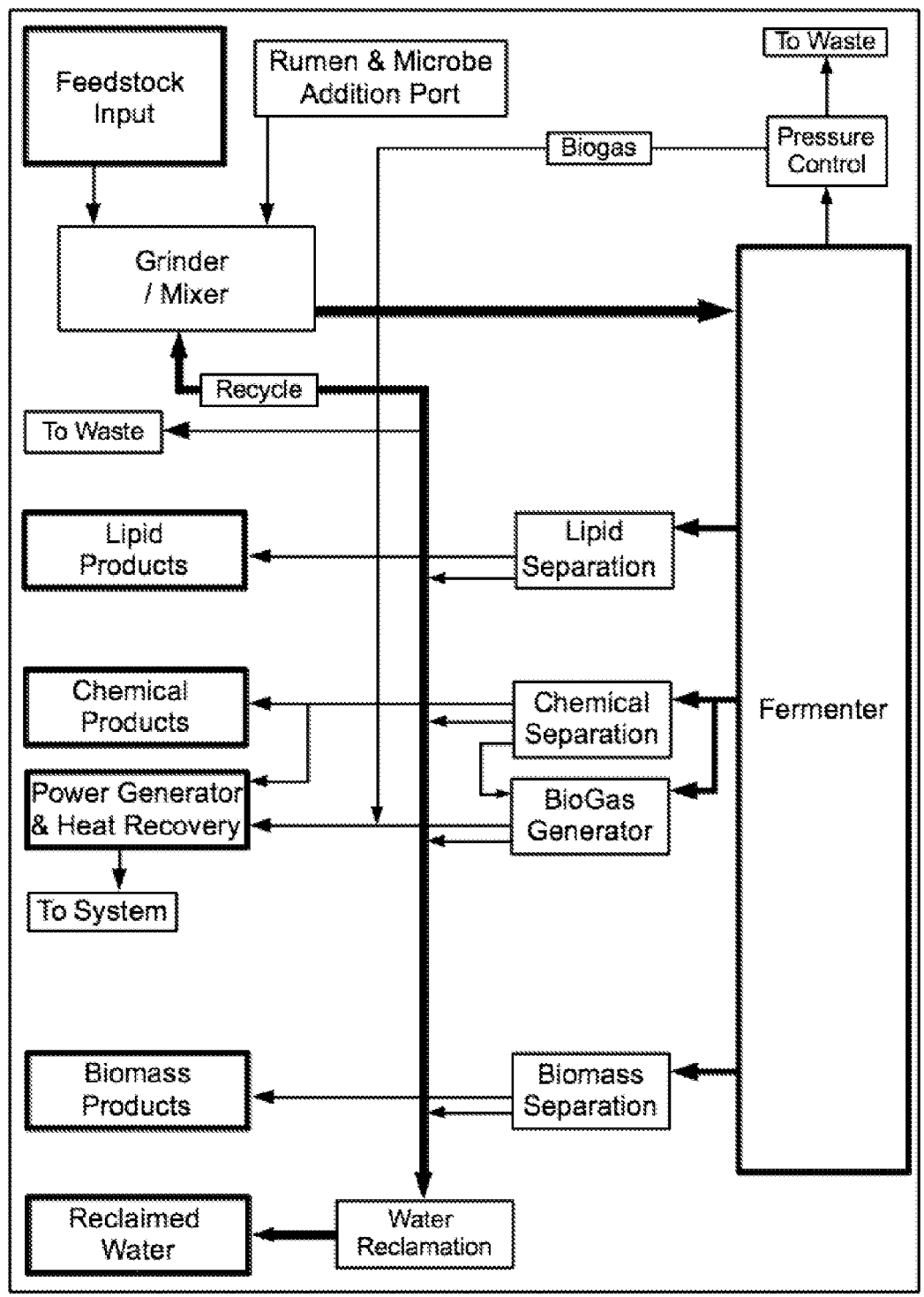
FIG. 3 is a flow diagram illustrating a Managed Ecosystem Fermentation (MEF) train for generating resources including chemical products, lipid products, biomass products, biogas, power and heat, and reclaimed water from fermentation of organic feedstocks with rumen. The MEF train allows for fractionation of the lipids, chemicals, biomass, and biogas from the fermenter.

Another embodiment is depicted in the flow diagram illustrated in FIG. 3. FIG. 3 shows a Managed Ecosystem Fermentation (MEF) train for generating resources including chemicals, lipids, biomass, biogas, power and heat, and reclaimed water from fermentation of the organic feedstock with the rumen. In this embodiment, the method comprises fractionating each of the lipids, chemicals, biomass, and biogas from the fermenter based on the physical properties of each resource. For example, the lipids float to the top of the fermentation liquid, the chemicals are soluble in the fermentation liquid, a significant portion of the biomass sinks to the bottom of the fermenter, and the biogas is in the gas phase. As illustrated in FIG. 3, the lipids are fractionated from the top section of the fermenter, the biomass is fractionated from the bottom section of the fermenter, the chemicals are fractionated from the middle section of the fermenter, and the gas is released from the top of the fermenter.

In one embodiment of the method of fermenting an organic feedstock with a rumen to generate a resource, the method comprises recycling the organic feedstock that is undigested through a grinder/mixer. This embodiment is illustrated in FIGS. 2 and 3.

In one embodiment of the method of fermenting an organic feedstock with a rumen to generate a resource, the method comprises re-inoculating the organic feedstock with the rumen. In one embodiment, the re-inoculating is periodic. The re-inoculating is performed using the rumen and microbe addition port illustrated in FIGS. 2 and 3.

In one embodiment of the method of fermenting an organic feedstock with a rumen to generate a resource, the method comprises removing a portion of the chemicals that are acidic to maintain the fermenting at a pH in a range between about pH 4 to about pH 9. In one embodiment, the pH range is between about pH 5 to about pH 8. In one embodiment, removing the acidic chemicals is continuous. In one embodiment, the acidic chemicals comprise VFAs.

In one embodiment of the method for fermenting an organic feedstock with a rumen to generate a resource, the method comprises employing a process to generate power and/or heat for the method, wherein the process utilizes at least a portion of the resource chemicals, the resource hydrogen, and/or the resource biogas.

In one embodiment of the method for fermenting an organic feedstock with a rumen to generate a resource, the method comprises reclaiming at least a portion of the generated resource water.

In one embodiment of the method for fermenting an organic feedstock with a rumen to generate a resource, the method comprises adding one or more of a microorganism, bacteria, butyric acid producing bacteria, cellulosic bacteria, *Clostridium acetobutylicium* bacteria, yeast, industrial yeast, brewer's yeast, *Trichoderma reesei*, fungi, protozoa, earth worm microbes, termite microbes, cecum microbes, rabbit cecum microbes, or horse cecum microbes, or combinations thereof.

In one embodiment of the method for fermenting an organic feedstock with a rumen to generate a resource, the method comprises separating one or more of the chemicals in a chemical separation unit. This embodiment is illustrated in FIGS. 2 and 3. In one embodiment, the chemicals comprise one or more of volatile fatty acids, long chain fatty acids, acetic acid, proprionic acid, isobutyric acid, butyric acid, isovaleric acid, valeric acid, lactic acid, or hexanoic acid, and the chemical separation unit comprises an ion exchange technology to effectuate separation of one or more of the chemicals.

In one embodiment of the method for fermenting an organic feedstock with a rumen to generate a resource, the method comprises separating the lipids from the biomass, the feedstock, and the water. This embodiment is illustrated in FIG. 3.

In one embodiment of the method for fermenting an organic feedstock with a rumen to generate a resource, one of the resources generated is chemicals, and the method comprises shunting at least a portion of the chemicals to a biogas generator, wherein the biogas generator is a second fermenter that comprises the rumen; and fermenting the chemicals and the rumen in the biogas generator to generate biogas. This embodiment is illustrated in FIG. 3. In one embodiment, the method comprises separating one or more of the chemicals in a chemical separation unit, wherein the separated chemicals comprise acetic acid, and shunting the separated acetic acid to the biogas generator. In one embodiment, the fermenting in the biogas generator is performed at a pH of above about pH 6.2 to select for generation of the resource biogas. In one embodiment, the method comprises employing the generated biogas from the biogas generator to power the method.

In one embodiment of the method for fermenting an organic feedstock with a rumen to generate a resource, one of the resources generated is chemicals and the comprises separating one or more of the chemicals in a chemical separation unit, wherein the separated chemicals comprise acetic acid; and shunting at least a portion of the separated chemicals comprising acetic acid to a ceramic oxide fuel cell process for generating power from the acetic acid; and utilizing the generated power in the method. This embodiment is illustrated in FIG. 3.

Figure 4:
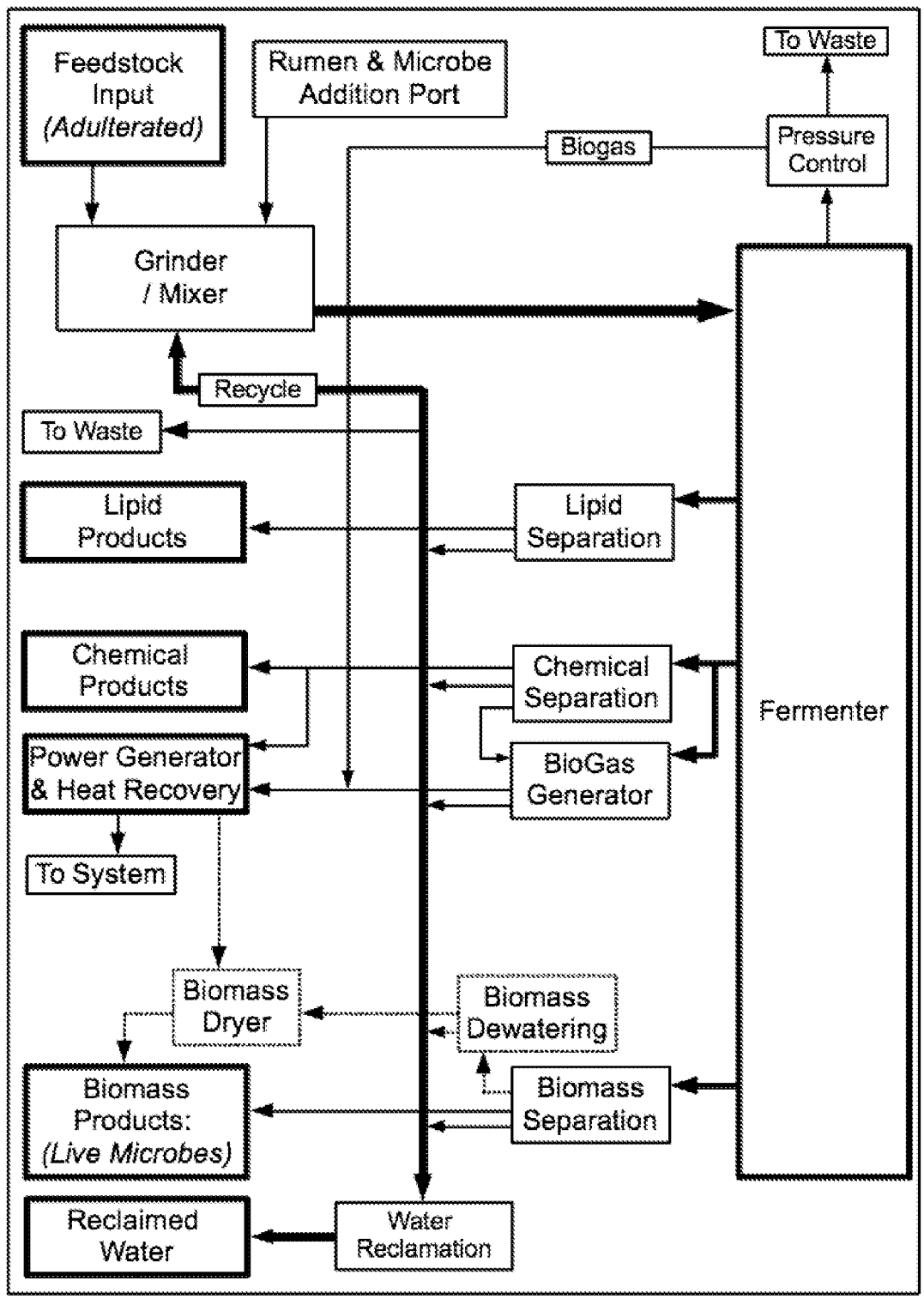
FIG. 4 is the same flow diagram as depicted in FIG. 3 except that it shows the use of adulterated feedstock to generate biomass to produce a soil enhancer having live microbes.
Figure 5:
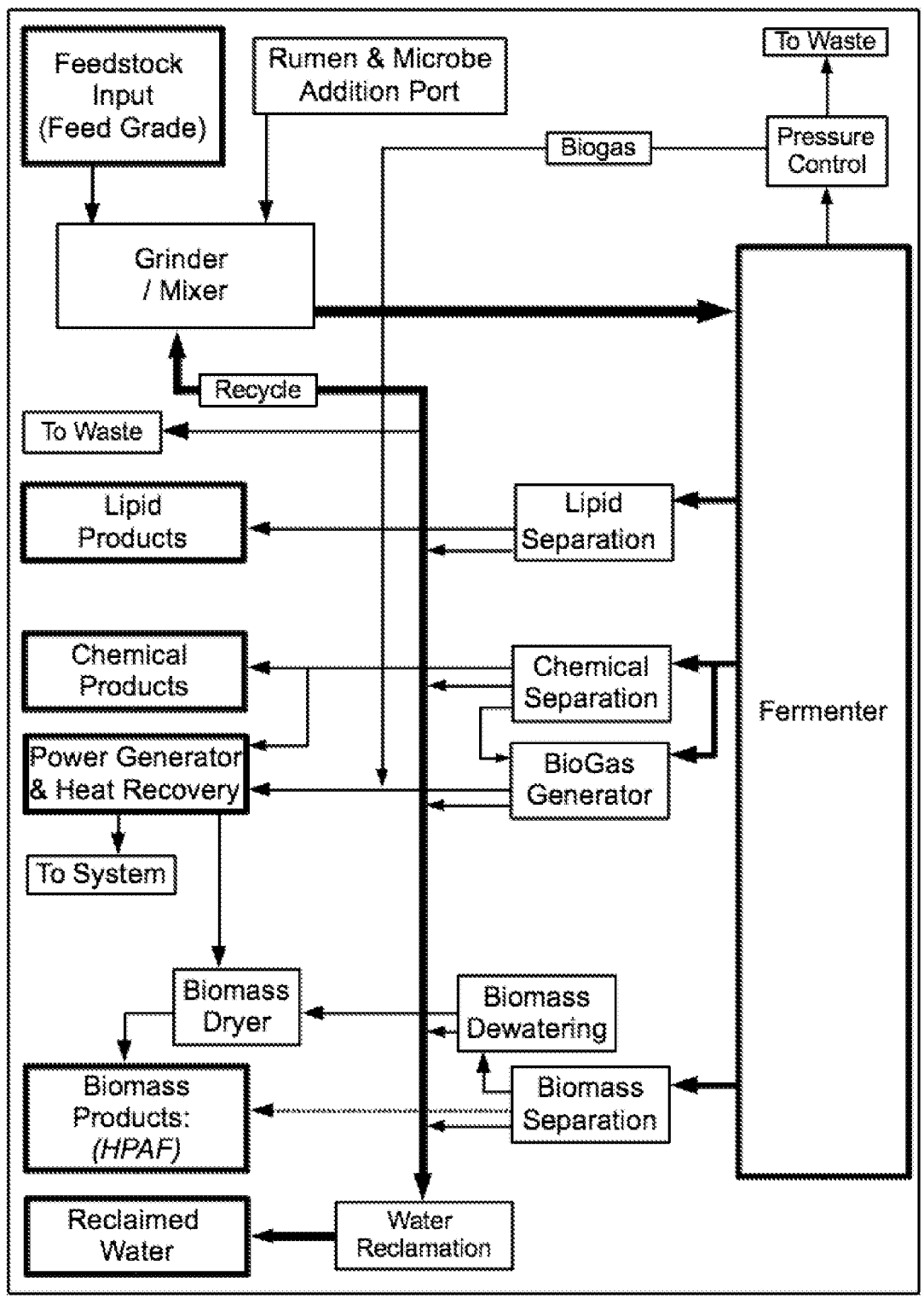
FIG. 5 is the same flow diagram as depicted in FIG. 4 with the addition that it shows the use of feed grade feedstock to generate biomass that is dewatered and dried to produce High Protein Animal Feed (HPAF).
Figure 6:
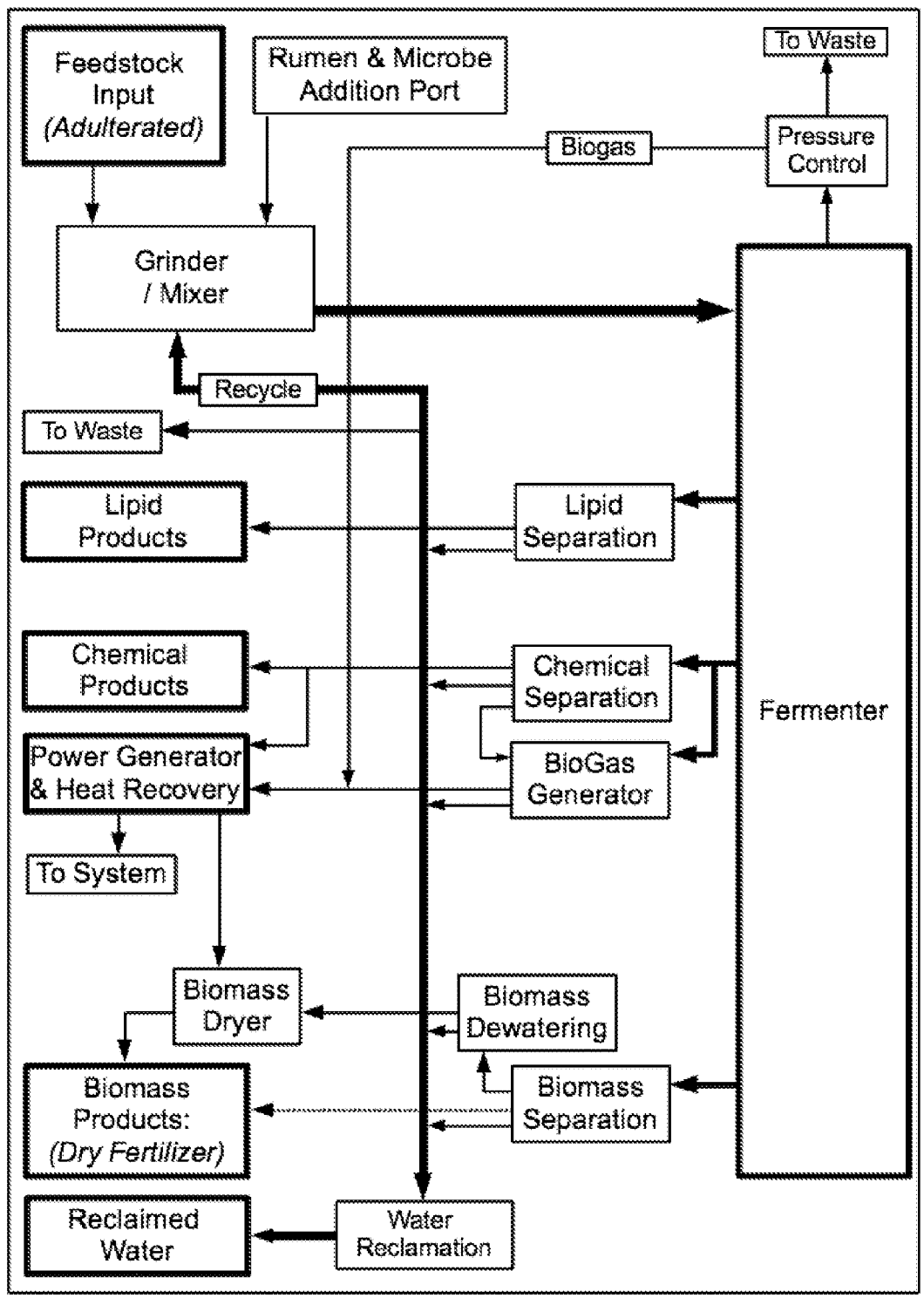
FIG. 6 is the same flow diagram as depicted in FIG. 5 except that it shows the use of adulterated feedstock to generate biomass that is dewatered and dried to produce dry fertilizer.

In one embodiment of the method for fermenting an organic feedstock with a rumen to generate a resource, the resource comprises biomass and the method comprises fractionating and/or separating the resource biomass using particulate separation and dewatering the biomass. This embodiment is illustrated in FIGS. 2 and 3. In one embodiment of the method, the organic feedstock is an adulterated feedstock and the dewatered biomass is a soil enhancer having live microbes. This embodiment is depicted in FIG. 4. In one embodiment, the method comprises utilizing at least a portion of one or more of the resources comprising chemicals, hydrogen, or biogas to generate power for the dewatering. In one embodiment, the method comprises drying the dewatered biomass. In one embodiment, the organic feedstock is a feed grade feedstock and the dewatered and dried biomass is a high protein animal feed (HPAF). This embodiment is depicted in FIG. 5. In one embodiment, the organic feedstock is an adulterated feedstock and the dewatered and dried biomass is a dry fertilizer. This embodiment is depicted in FIG. 6. In one embodiment, the method comprises utilizing at least a portion of one or more of the resource chemicals, resource hydrogen, or resource biogas that are generated to generate power and/or heat for the dewatering and drying.

In one embodiment of the method for fermenting an organic feedstock with a rumen to generate a resource, the method comprises applying a process for growing algae with the carbon dioxide produced by the method.

In one embodiment of the method for fermenting an organic feedstock with a rumen to generate a resource, the fermenting is not performed under sterile conditions.

In one embodiment of the method for fermenting an organic feedstock with a rumen to generate a resource, the method comprises adding one or more substances capable of being utilized as a source of nitrogen in the fermenting. In one embodiment, the substance is selected from the group consisting of ammonia, urea, amino acids, and amines, and combinations thereof.

In one embodiment of the method for fermenting an organic feedstock with a rumen to generate a resource, the feedstock comprises catering waste and the rumen comprises bovine rumen.

In one embodiment, the feedstock comprises catering waste and the rumen comprises bovine rumen and the method comprises adding ammonia. In one embodiment, the feedstock comprises catering waste, the rumen comprises bovine rumen, and the feedstock further comprises biodiesel waste. In one embodiment, the rumen further comprises sheep rumen. In one embodiment, the feedstock comprises catering waste, the rumen comprises bovine rumen, and the method comprises adding a butyric acid producing bacteria. In one embodiment, the butyric acid producing bacteria is *Clostridium acetobutylicum* bacteria.

In one embodiment of the method for fermenting an organic feedstock with a rumen to generate a resource, the resource comprises lipids, chemicals, biogas, and biomass, and the method comprises fractionating and/or separating through particulate separation the resource lipids, chemicals, biogas, and biomass; and producing one or more of a chemical product, a lipid product, a biogas, a biomass product, a fertilizer, a high protein animal feed, a soil enhancer with live microbes, acetic acid, proprionic acid, isobutyric acid, butyric acid, isovaleric acid, valeric acid, lactic acid, or hexanoic acid, or combinations thereof. In one embodiment, the organic feedstock comprises algae and the lipid product is produced.

In one embodiment of the method for fermenting an organic feedstock with a rumen to generate a resource, the method comprises monitoring and/or controlling the fermenting from a remote facility, wherein the monitoring and/or controlling is effectuated through use of a communications link between the fermenting and the remote facility. In one embodiment of the method, the communications link comprises a cabled or wireless technology.

In one embodiment, the presently disclosed subject matter provides a resource generated according to the method provided herein, the method comprising fermenting an organic feedstock with a rumen to generate the resource. The resource provided is selected from the group consisting of chemicals, lipids, volatile fatty acids, long chain fatty acids, acetic acid, proprionic acid, isobutyric acid, butyric acid, isovaleric acid, valeric acid, lactic acid, hexanoic acid, biomass, high protein animal feed, fertilizer, phosphate fertilizer, nitrogen fertilizer, proteins, amino acids, lysine, enzymes, cellulase, alpha-amylase, histidase, lysozyme, penicillin acylase, ethanol, butanol, biogas, methane, hydrogen, carbon dioxide, and water, and combinations thereof.

In one embodiment, the presently disclosed subject matter provides a system comprising a grinder/mixer configured to receive the organic feedstock and the rumen, and a fermenter configured to receive the organic feedstock and the rumen, and the fermenter configured to ferment the organic feedstock to generate a resource. This embodiment is illustrated in FIGS. 2-7 and 9-11. In one embodiment of the system, the fermenter is configured to recycle the organic feedstock that is undigested through the grinder/mixer. In one embodiment of the system, the grinder/mixer is configured for re-inoculation of the organic feedstock with the rumen. In one embodiment of the system, the re-inoculation is periodic.

In one embodiment of the system configured to ferment the organic feedstock with the rumen to generate a resource, the system comprises a power generator configured to utilize at least a portion of the resource chemicals, the resource hydrogen, and/or the resource biogas to generate power and/or heat for the system. In one embodiment, the system comprises a water reclamation unit.

In one embodiment of the system configured to ferment the organic feedstock with the rumen to generate a resource, the fermenter is configured to stir and/or agitate the organic feedstock and rumen during the fermentation. In one embodiment, the resource comprises chemicals and biomass, and the system comprises a particulate separation unit configured to separate the chemicals from the biomass. This embodiment is illustrated in FIG. 2.

In one embodiment of the system for generating resources from feedstocks, the fermenter is configured to fractionate one or more of the resources selected from the group consisting of lipids, chemicals, biogas, and biomass. This embodiment is illustrated in FIG. 3.

In one embodiment of the system for generating resources from feedstocks, the resource comprises chemicals and the fermenter is configured for removal of a portion of the chemicals that are acidic to maintain the pH of the fermentation in a range between about pH 4 to about pH 9. In one embodiment, the pH of the fermentation is maintained in a range between about pH 5 to about pH 8. In one embodiment, the fermenter is configured for the removal of the chemicals in a continuous manner. In one embodiment, the acidic chemicals that are removed comprise VFAs.

In one embodiment of the system for generating resources from feedstocks, the grinder/mixer is configured to receive one or more of a microorganism, a bacteria, a butyric acid producing bacteria, a cellulosic bacteria, a *Clostridium acetobutylicum* bacteria, a yeast, an industrial yeast, a brewer's yeast, a *Trichoderma reesei*, a fungi, a protozoa, earth worm microbes, termite microbes, cecum microbes, rabbit cecum microbes, or horse cecum microbes, or combinations thereof.

In one embodiment of the system configured to ferment the organic feedstock with the rumen to generate a resource, the system comprises a chemical separation unit configured to separate one or more of the chemicals. In one embodiment of the system, the chemicals comprise one or more of volatile fatty acids, long chain fatty acids, acetic acid, proprionic acid, isobutyric acid, butyric acid, isovaleric acid, valeric acid, lactic acid, or hexanoic acid, and the chemical separation unit comprises an ion exchange technology. In one embodiment, the system comprises a lipid separation unit configured to separate the lipids from the biomass, the feedstock, and the water.

In one embodiment of the system configured to ferment the organic feedstock with the rumen to generate a resource, the resource generated comprises chemicals, and the system comprises a biogas generator configured as a second fermenter to receive the rumen and at least a portion of the chemicals to generate biogas. In one embodiment of the system, the chemicals comprise acetic acid and the system comprises a chemical separation unit configured to separate at least a portion of the acetic acid, wherein the separated acetic acid is shunted to the biogas generator. In one embodiment of the system, the biogas generator is maintained at a pH of above about pH 6.2. In one embodiment of the system, the generated biogas is employed to power the system.

In one embodiment of the system configured to ferment the organic feedstock with the rumen to generate a resource, the resource generated comprises chemicals and the system comprises a chemical separation unit configured to separate one or more of the chemicals, wherein the separated chemicals comprise acetic acid, and a ceramic oxide fuel cell unit configured to receive and to generate power from the separated acetic acid, wherein the generated power is utilized in the system.

In one embodiment of the system configured to ferment the organic feedstock with the rumen to generate a resource, the system comprises a particulate separation unit configured to separate the biomass or the fermenter is configured to fractionate the biomass; the system comprises a biomass separation unit; and the system comprises a biomass dewatering unit configured to dewater the biomass. In one embodiment of the system, the organic feedstock is an adulterated feedstock and the dewatered biomass is a soil enhancer having live microbes. This embodiment of the system is depicted in FIG. 4. In one embodiment of the system, the system comprises a power generator configured to utilize at least a portion of one or more of the generated resources comprising chemicals, hydrogen, or biogas to generate power for the dewatering. In one embodiment, the system comprises a biomass drying unit configured to dry the dewatered biomass. In one embodiment of the system, the organic feedstock is a feed grade feedstock and the dewatered and dried biomass is a high protein animal feed (HPAF). This embodiment of the system is depicted in FIG. 5. In one embodiment of the system, the organic feedstock is an adulterated feedstock and the dewatered and dried biomass is a dry fertilizer. This embodiment of the system is depicted in FIG. 6. In one embodiment, the system comprises a power generator configured to utilize at least a portion of one or more of the generated resources comprising chemicals, hydrogen, or biogas to generate power for the dewatering and/or drying.

In one embodiment of the system configured to ferment the organic feedstock with the rumen to generate a resource, the system comprises an algal growth unit configured for growing algae with the generated resource carbon dioxide.

In one embodiment of the system configured to ferment the organic feedstock with the rumen to generate a resource, the system is not configured to be operated under sterile conditions.

In one embodiment of the system configured to ferment the organic feedstock with the rumen to generate a resource, the grinder/mixer is configured to receive to receive one or more substances capable of being utilized as a source of nitrogen in the fermenting. In one embodiment of the system, the substance is selected from the group consisting of ammonia, urea, amino acids, or amines, or combinations thereof.

In one embodiment of the system configured to ferment the organic feedstock with the rumen to generate a resource, the organic feedstock comprises catering waste and the rumen comprises bovine rumen. In one embodiment of the system, the organic feedstock comprises catering waste, the rumen comprises bovine rumen, and the mixer/grinder is configured to receive addition of ammonia. In one embodiment of the system, the organic feedstock comprises catering waste, the rumen comprises bovine rumen, and the organic feedstock comprises biodiesel waste. In one embodiment of the system, the organic feedstock comprises catering waste and the rumen comprises a mixture of bovine rumen and sheep rumen. In one embodiment of the system, the organic feedstock comprises catering waste, the rumen comprises bovine rumen, and the mixer/grinder is configured to receive addition of a butyric acid producing bacteria. In one embodiment of a system, the butyric acid producing bacteria is *Clostridium acetobutylicium* bacteria.

In one embodiment of the system configured to ferment the organic feedstock with the rumen to generate a resource, the resource comprises chemicals, biomass, lipids, and biogas, and the system comprises the fermenter configured to fractionate the resource chemicals, biomass, lipids, and biogas; a chemical separation unit configured to generate a chemical product; and a biomass separation unit configured to generate a biomass product. This embodiment is illustrated in FIG. 3. In one embodiment of the system, the system comprises a biogas generator configured to generate biogas from at least a portion of the chemicals. In one embodiment of the system, the system comprises a lipid separation unit configured to generate a lipid product. In one embodiment of the system, the feedstock comprises algae and the lipid product is the lipid from the algae. In one embodiment of the system, the chemical product comprises an acetic acid, a proprionic acid, an isobutyric acid, a butyric acid, an isovaleric acid, a valeric acid, a lactic acid, or a hexanoic acid, or combinations thereof. In one embodiment of the system, the biomass product is selected from the group consisting of a fertilizer, a high protein animal feed, and a soil enhancer having live microbes. This embodiment is illustrated in FIGS. 4-6. In one embodiment, the system comprises a power generation and heat recovery unit configured to generate power and/or heat, wherein the generated power and/or heat are utilized in the system.

In one embodiment of the system configured to ferment the organic feedstock with the rumen to generate a resource, the system comprises a remote facility configured to monitor and/or control the fermenter through use of a communications link between the remote facility and the fermenter. In one embodiment of the system, the communications link is configured as a cabled or a wireless technology.

Figure 7:
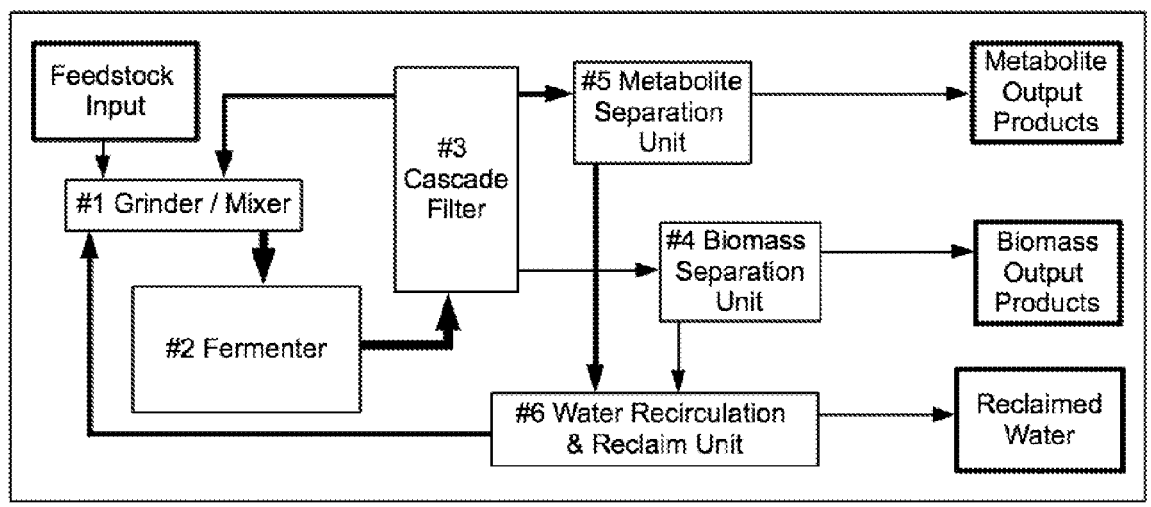
FIG. 7 is a flow diagram illustrating a Managed Ecosystem Fermentation (MEF) train. In the MEF train, the metabolites and microbial mass produced by fermentation of the feedstock by microbes are recovered as biomass products, metabolite (chemical) products, and reclaimed water.

One embodiment of the presently disclosed subject matter is a process for preparing and biologically converting organic waste and/or other organic materials into chemicals, biomass and residual materials, then recovering multiple products, plus reclaimed water. The general process is shown in FIG. 7.

The biological process uses an ecosystem approach employing dozens to thousands of species of microorganisms that provides greater flexibility to handle heterogeneous waste streams (i.e., waste streams of more than a single type of waste) than traditional fermentation systems and higher levels of specificity of product output than anaerobic digestion systems. This process is called Managed Ecosystem Fermentation (MEF). In one embodiment, the chemicals and biomass materials are recovered from the process and separated by particle size into multiple streams for processing.

One embodiment of the disclosed subject matter is the process for control and management of the feedstock materials to maintain desired properties within the MEF, the chemicals, the biomass or the residuals. An example of this embodiment would be the blending of two or more feedstock materials (or additive materials); such as sewage sludge and yard waste or municipal solid waste; to obtain the desired carbon-to-nitrogen ratio, pH or other properties of the blend that could improve fermentation efficiency.

One embodiment of the disclosed subject matter is the process for the extraction of chemicals from the MEF process fluids to maintain pH conditions within the MEF vessel or to extract specific materials from the chemicals. Most of the liquid chemicals from MEF will be volatile fatty acids; as acetate, propionate and butyrate. The chemicals also contain small fractions of longer chain fatty acids and carboxylic acids. In one embodiment, the chemicals are separated in a chemical separation unit. In one embodiment, chemical separation is effectuated using ion exchange technology. The ion exchange technology can include, for example, the use of an anion exchange matrix known to those of skill in the art to bind and recover carboxylic acids such as, for example, the VFAs in the fermentation broth. In one example the anion exchange matrix is a fluidized bed anion exchange matrix. In one embodiment, the first step is to remove some fraction of the fermentation broth from the MEF vessel and filter the removed broth by size exclusion to remove feedstock materials and most biomass materials from the remaining liquid fraction; such that the remaining liquid consists or comprises mostly the chemicals, buffers, and water. In one embodiment, the second step is the removal of the chemicals from the water and buffer solution, such that the buffers are restored and pH of the solution is raised to the desired value for recirculation back into the fermentation.

In one embodiment, at least a portion of the removed chemicals are shunted to an additional microbial fermentation tank configured as a biogas generator to convert the VFAs in the filtered liquid solution into methane and carbon dioxide using methanogenic microbes. This embodiment is illustrated for example in FIGS. 3-6 and 9-11. These methanogenic microbes convert acetate and other volatile fatty acids in the mixed liquid solution into a methane and carbon dioxide, gas phase materials that may be easily separated by gravity from the remaining liquids. In one embodiment, the methanogenic bacteria are present in the rumen and the generation of biogas is selected for in the biogas generator by maintaining the pH in the biogas generator above about pH 6.2. Other processes for removing the chemicals from the filtered fermentation broth can be employed in this embodiment of controlling the MEF process.

One aspect of the presently disclosed subject matter is the process method for separating specific protein species from the fermentation broth using a series of specialized filter materials, each prepared to capture only one protein (or enzyme or amino acid). These filter materials can have the substrate form of textiles, membranes, beads, or other solid material. This substrate material is treated to form many ligand sites that will anchor one of many specific "capture" compounds, each of which can bind one of the molecules of interest from the fermentation broth. The substrate, ligand and capture chemical together form a filtering material which allows the fermentation fluid to intimately contact the capture compound sites, for the purpose of binding the target protein material and effecting its removal from the fermentation fluid.

Figure 12:
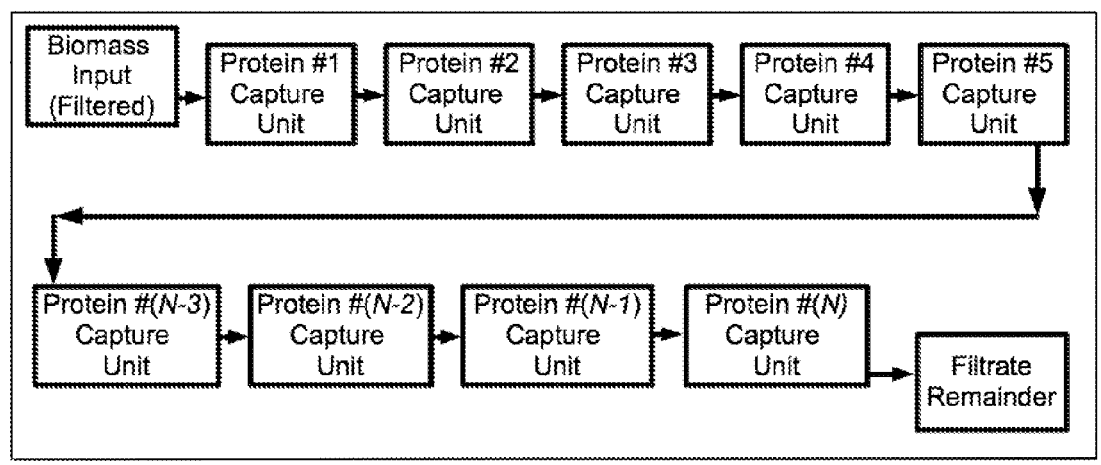
FIG. 12 is a flow diagram illustrating the separation of different protein species using a series of capture units.

In one embodiment of the presently disclosed subject matter, functionalized filters are utilized in a series flow arrangement to capture one or more proteins from the MEF (see, e.g. US Patent Publication No. 2007/0161308). In this embodiment, many filters are arranged in a series flow arrangement, where each filter or set of filters is functionalized to bind a different protein (FIG. 12). The purpose of this arrangement is to extract different protein species from a common fermentation fluid, such that each protein species is captured on a separate filter or set of filters.

This embodiment is different from U.S. Pat. No. 7,285,219 titled "Chromatographic separation member and method," in that the substrate is not a solid film, but may be beads or a textile felt with much greater surface area. While this embodiment can use the principle of repeatedly removing single protein species from a fluid mixture with a material assembly that can bind the protein of interest or using displacement chromatography, both apparently used in U.S. Pat. No. 7,285,219, the substrate need not be a polymer film, as required in said patent. Another difference in this embodiment and said patent is that the binding chemical and release agents can utilize a different chemical principle, other than chromatography.

One embodiment of the presently disclosed subject matter is the process method for custom blending of additional species of naturally occurring microbes into an existing ecosystem of natural microbes that is already living symbiotically inside a mechanically maintained environment. The blending microbes can be another microbial ecosystem, multiple ecosystems, single species of microbe or small set of microbial species. The purpose of this microbial blending is to enhance specific properties of the managed ecosystem fermentation process. These additional properties can be for consumption of specific compounds in the feedstock material, or production of specific chemicals, or production of specific biomass proteins, or preservation of specific compounds from the feedstock within the fermentation fluid. In one embodiment, the microbial blending can be by adding to the fermentation one or more of a microorganism such as, for example, a bacteria, a butyric acid producing bacteria, a cellulosic bacteria, a *Clostridium acetobutylicium* bacteria, a yeast, an industrial yeast, a brewer's yeast, a *Trichoderma reesei*, a fungi, a protozoa, earth worm microbes, termite microbes, cecum microbes, rabbit cecum microbes, or horse cecum microbes.

One embodiment of the presently disclosed subject matter is the ability to distribute many MEF systems in a region and control them from a central location. This aspect is one feature of a manufacturing system architecture called Distributed, Integrated Biochemical Manufacturing (DIBM). The MEF process equipment (the Remote Conversion Unit, RCU) is located at the point of feedstock concentration such that transportation expense of raw materials is reduced. Each RCU is connected to a Central Facility (CF) by a communications link that can include any cabled or wireless technology with adequate bandwidth and range. The central control room has direct monitoring and control over each RCU within its assigned region. Personnel in the central control room will dispatch workers to the RCUs for normal operations, maintenance and emergency tasks. This architecture centralizes the monitoring tasks because MEF processes usually change slowly, but any chemical or biological process does need a minimum level of monitoring at all times.

Control can be passed to more remote control rooms in other regions or a central office as desired, creating the opportunity for redundant monitoring and control capabilities, as a safety system.

Labor assignments can be optimized to minimize response time or miles driven. Sharing both skilled operators and maintenance personnel between a large number of sites can increase labor utilization rates and apply high skill levels when and where needed.

Material collection routes for routine operations can be established to minimize miles driven per ton of material collected.

One embodiment of the presently disclosed subject matter is the ability of the Central Facilities to integrate the output materials from many RCUs, which may be utilizing different sources of adulterated feedstocks. This embodiment does not implement any mixing of adulterated materials into any feed grade materials. Separating the adulterated and feed grade material classes is necessary for animal safety and regulatory compliance. This aspect is a feature of the DIBM manufacturing system architecture. Because MEF processes produce common chemicals, some common proteins, and other fungible products, the DIBM system architecture can aggregate the fungible materials at the CF for further processing. The advantage of DIBM is the economies of scale it provides in manufacturing secondary products from the RCU products, while minimizing transport cost of raw materials for initial conversion.

Not all materials must flow from the RCU to the CF. Where the products of particular RCUs are not fungible, such as animal feed or other feed grade production, these products may be delivered directly to local customers, such as sending the animal feed product directly to a feed mill.

One embodiment of the presently disclosed subject matter is the product of a low moisture High Protein Animal Feed (HPAF) that can be used in the diets of farm animals. This material is fed to animals, so the feedstock must be feed grade materials. The MEF produces the protein for this material from the carbohydrates, often including cellulose, found in the feedstock material. The physical and nutritional properties can be adjusted for blending into the dry diet of the animal populations. It is expected that the HPAF will have a protein concentration between 10% and 50% depending on local conditions and customer preference. It is expected that the physical format of HPAF will be dried pellets, similar to dog kibble, to reduce dusting during shipment and improve blending properties for the feed mill. Other form factors for this material can be considered.

One embodiment of the presently disclosed subject matter is the product of an animal feed flavoring agent that is added to feed mixtures to improve the palatability of other materials. This material is fed to animals, so the feedstock must be feed grade materials. The MEF process produces the biomass for this material from the carbohydrates, often including cellulose, found in the feedstock material. This material is the concentrated biomass extract from the fermentation, containing a high density of the microbes and enough liquids to remain easily handled. Chemical liquids may be included in this material. The material is heated and/or oxygenated adequately to kill the microbes and ensure product safety.

One embodiment of the presently disclosed subject matter is the product of a low moisture pelletized fertilizer product that provides an organic source of nitrogen and phosphorous. This material is not intended to be used as animal feed or to be applied to growing crops, so it may be manufactured from adulterated organic materials. The MEF process produces the biomass for this material from the carbohydrates, often including cellulose, found in the feedstock material. The biomass is dried and thermally denatured so that the protein in the biomass will become bio-available nitrogen, phosphorus and organic matter for plants. The physical properties and packaging of this material can be adjusted to suit local markets.

One embodiment of the presently disclosed subject matter is the product of living anaerobic microbes that can be incorporated into soils to enhance and reinforce the endogenous microbial populations. The purpose for this material is to improve plant yields by enhancing microbial activity in the soil. The form of this material is an anaerobic liquid slurry that is incorporated into the soil below the surface to limit oxygen exposure during application.

One embodiment of the presently disclosed subject matter is the detoxification of specific organic agents. For example, cattle have demonstrated that rumen is able to detoxify certain organic compounds, including aflatoxin. In another example, research with Australian sheep has demonstrated that the ability to digest specific tannins can be acquired by animals receiving additional rumen microbes. Another example is research showing that *Escherichia coli* are displaced in rumen and only found in very small numbers in rumen. Accordingly, in one embodiment, the MEF process can be utilized as a disposal method for organic agents that will be tested and identified.

In one embodiment, a method is provided for a detoxification service where the customer brings the material to an operating MEF site that has demonstrated the capability to denature or destroy the chemical and/or organic agent in question. In another embodiment, a method is provided for a specific set of microbe species to be installed in a non-MEF ecosystem fermentation, such as a wastewater treatment plant for the purpose of adding the microbial capacity to denature or consume specific organic targets that were not sufficiently treated by the original ecosystem. Target agents for consumption include estrogens in wastewater and pharmaceutical compounds in wastewater. Microbial sets for this embodiment are developed using the technology described herein.

The equipment described in this section is shown in FIG. 7, which illustrates a general process diagram for an MEF train according to the presently disclosed subject matter. These "Units" are blocks of equipment that may contain multiple elements to perform the tasks.

Unit 1, Grinder Mixer.

This equipment performs three tasks before sending the slurry to the fermenter: 1) reduce the feedstock to a range of sizes appropriate for the fermentation; 2) introduce the recirculated buffer solution and the inoculating microbes to the feedstock; and 3) provide proper mixing and water dilution between the feedstock and recirculation fluids.

The initial size reduction to a top size of about 5 cm is a coarse grind and approximates the initial mastication of cattle during grazing. The large top size during the first pass will minimize the energy required for size reduction. As materials are recycled back to the grinder-mixer from the cascade filter, their size will be further reduced by passing through the grinder again. The energy requirement for the second and subsequent passes will be lower as a result of the initial enzyme attack on the fibers. This equipment will have a water jacket as necessary to bring the slurry to the operating temperature of the fermenter.

The feedstock mixing with buffer, water and microbes will form a slurry with the proper solids content, pH and inoculation to initiate fermentation of the feedstock. The final step within the grinder mixer unit is to pump the slurry into the fermenter with sufficient velocity to rapidly mix the slurry into the fermentation broth.

Unit 2, Fermenter.

This equipment provides the residence time and controlled conditions for the microbial ecosystem within the Unit to digest the feedstock materials into chemicals, biomass and residual materials.

The controlled environmental factors within this unit may include residence time, agitation shear rate, temperature, fluid pH, redox potential, headspace atmospheric composition and pressure. Each of these values can be measured in the fermenter or nearby piping and connected to a central monitoring and control network. The specific value of each control point will depend on the feedstock, the constituent makeup of the microbial ecosystem, and the product mix desired at the outputs. The ability to influence the output chemistry by manipulating the inputs and control points is an important feature of MEF that demonstrates the flexibility of the processes.

System residence is calculated on the time elapsed in the grinder-mixer, fermenter, and cascade filter units and associated piping. The residence time within the system is different for liquids and solids. Liquid residence time is based on the rate of chemical production and buffer content because the pH of the broth has to remain in control, typically a value between 5.5 and 7.0. As fermentation rates increase, the liquid residence time will decrease, which increases the chemical removal rate to maintain the pH setpoint.

The residence time for the solids in the system will depend on particle size and other factors, such as the solids blowdown rate, used for removal of indigestible materials. In most ruminants, the solids residence time is between 1 and 3 days, depending on the animal species and their diet. Solids residence time for MEF processes is expected to be similar to the rumen process because similar microbes are the driving force for solids reduction in both cases.

Unit 3, Cascade Filter.

Figure 8:
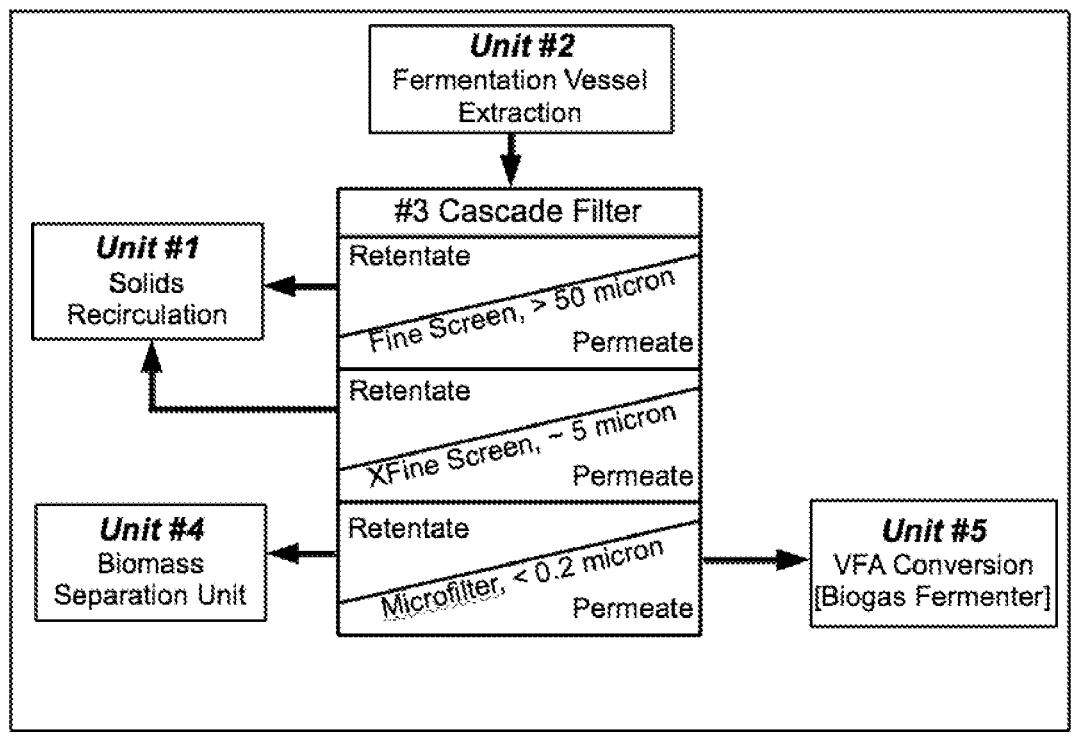
FIG. 8 is a flow diagram illustrating a cascade filter unit comprising a set of membranes arranged in order of descending pore size. The first screens are for retaining the larger pieces of digesta for return to the fermentation system. The later screens enable separation between the biomass and the metabolites (chemicals) extracted from the fermentation.

This unit consists or comprises of a set of membranes, arranged in order of descending pore size, as shown in FIG. 8. Each membrane of the cascade is in a cross-flow geometry, with adequate retentate flow to minimize the cake buildup on the membrane. The total number of membranes will depend on the caking characteristics of the fermentation and is expected to vary with different feedstocks and microbial ecosystems. The expected minimum screen set would include retaining the larger pieces of digesta for return to the fermentation system. There may be several screens in this set, depending on the particle size distribution and caking characteristics of the fermentation materials. These physical properties of the fluid will determine the number of screens, the pore sizes required and the necessary tangential flow rates for proper operation. These values will be determined empirically for each major type of feedstock encountered but the minimum pore size is expected to be approximately 5 microns. All of the flow retained on the screens of the first stage will be recirculated back to the Unit 1 Grinder-Mixer.

The second set of screens is an important design element of the MEF train as it allows the initial separation between the biomass and the chemicals extracted from the fermentation, so that each of these materials can be processed independently for greater total revenue. This pore size is below the larger particles of incompletely digested feedstock and larger than the molecular size of the chemical chemicals, so that most of the solids from the biomass materials are retained on the membrane.

The task of the second set of screens is to capture the particulate material that passes the first set of screens and is retained on the second, where the second screen set may have a minimum size of 0.2 microns, in order to retain cells, cell debris, proteins, enzymes and amino acids from the fermentation. The material retained on these screens, including enough fluid to transport this material easily, is conveyed to Unit #4, the biomass separation unit.

The material passing the second set of screens is the water, buffering salts and the chemical chemicals as volatile fatty acids (VFAs) and longer chain carboxylic acids ($C_5$ to $C_{21}$), from the fermentation fluid. These materials are sent to Unit #5 for chemical processing into output products.

Unit 4, Biomass Separation.

This unit receives flow of mixed biomass from the Unit 3 Cascade Filter. This unit will process the mixed biomass into output products that can be transported from the site. Several different technologies can be incorporated into this unit, depending on the feedstock available and products desired.

Because the technology of this unit depends on the feedstock and products selected, the equipment details of this unit are listed in each of the examples below.

Unit 5, Chemical Separation.

This unit receives flow from Unit 3 that has passed a microfiltration level, so that there are few particulates, such as microbial biomass, within this stream. The major components of this stream are water, dissolved buffer salts, VFAs, and longer chain carboxylic acids that are the dominant chemical compounds produced by most microbial ecosystems described herein. This unit will reduce the concentration of VFAs and other chemicals so that the buffer is restored, raising the pH of the fluid leaving the unit. In one embodiment, the VFAs removed from the fermentation are converted to carbon dioxide and methane by the known technology of biogas fermentation using methanogenic microbes. In one embodiment this takes place in a biogas generator. In one embodiment, the removed chemicals are separated in the chemical separation unit using an ion exchange technology. The ion exchange technology can include, for example, the use of an anion exchange matrix known to those of skill in the art to bind and recover carboxylic acids such as, for example, the VFAs in the fermentation broth. In one example the anion exchange matrix is a fluidized bed anion exchange matrix. For example, in one embodiment acetic acid is separated from other VFAs, and the acetic acid is shunted to the biogas generator for biogas fermentation as described above. Other technologies may be employed in this unit as new processes surpass the economies of biogas processes.

Unit 6, Water Recirculation and Reclaim.

This unit receives the remainder flows from Units 4 & 5. This unit will maintain the total water balance on the system, separating and removing enough water from the remainder flows to balance the water entering the system in the feedstock. The core device in this unit is a reverse osmosis type membrane that is capable of separating the buffer salts from water. The buffer salts are concentrated and recycled within the process, remaining in the flow returned to Unit 1. The reclaimed water that passes the membrane will be expelled from the system and can be used for other purposes outside the system.

EXAMPLES

Example 1

Figure 9:
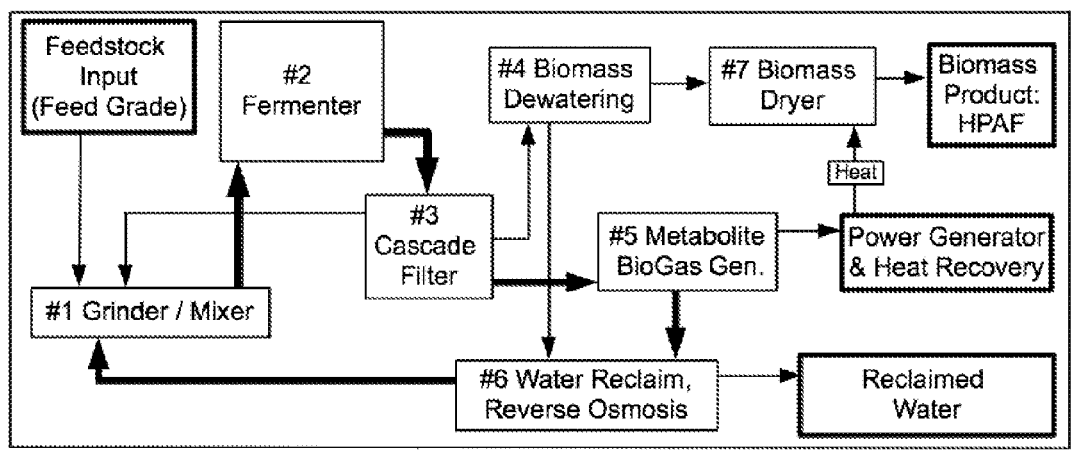
FIG. 9 is a flow diagram illustrating a Managed Ecosystem Fermentation (MEF) train for conversion of a feed grade feedstock to biomass that is dewatered and dried to produce High Protein Animal Feed (HPAF).

The processing of fruits and vegetable into food for human consumption produces a large quantity of byproduct organic waste that is rated "feed grade" and fit for animal consumption. The MEF process described herein can be utilized to convert the carbohydrates and cellulose into protein and provide reclaimed water to the host facility. The MEF process will reduce the mass of material to be transported as animal feed by 70% to 95%, significantly reducing transportation costs. The diagram of this process is shown in FIG. 9.

To produce High Protein Animal Feed (HPAF) from fruit and vegetable processing scraps, the MEF process will be used and supplemented by two additional processes. The chemicals would be removed in a biogas generator and the subsequent methane used to provide power and heat for operating the process. The biomass material would be dewatered, pelletized and dried to a moisture level expected in the trade, typically 12%. This material would have the size and texture of dry pet food to minimize dust losses and provide the expected mixing properties for the trade.

The biogas generator can be any of several commercial units capable of converting VFAs into methane using the methanogenic archaea or other methanogenic bacteria. A commercial upflow anaerobic sludge blanket (UASB) reactor is expected to provide the highest rate of gas production for the size equipment required. These units are also provide adequate clarification for the liquid entering the water recycle and recovery unit.

The Unit 4 biomass separation unit in this example could be assembled from commercial equipment. The first step would be a belt press or similar device to increase the solids content of the biomass from 5% up to approximately 20% to 30%. The second step in this unit is a pelletizing unit as used for cereal or pet food, followed by a hot air dryer to reduce the moisture content of the pellets to the desired level.

Example 2

A second product can be manufactured from the feed grade material using the same equipment train as shown in FIG. 9. By removing the biomass at a point in the process before it has been fully dried or denatured, it forms a separate product that can be utilized as a flavoring agent in animal feed. Certain species are attracted to this microbial mixture and this agent will improve palatability of other foods in the animal's diet. Observation has shown that dogs are strongly attracted to this material as it is removed from the reactor.

Example 3

Figure 10:
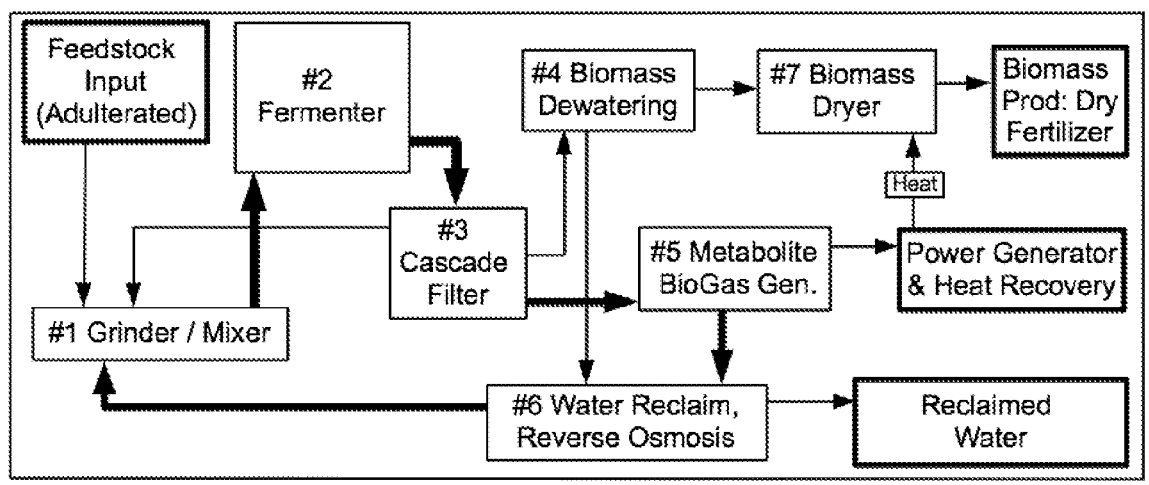
FIG. 10 is a flow diagram illustrating a Managed Ecosystem Fermentation (MEF) train for conversion of an adulterated organic waste feedstock to biomass that is dewatered and dried to produce a dried fertilizer with high levels of organics, nitrates, and phosphates.

There are many industrial and municipal processes that produce a large quantity of adulterated organic wastes that are not acceptable for any product sold for animal consumption. These organic waste sources may include beef slaughterhouse wastes, the organic fraction of municipal solid waste (OF-MSW), sewage sludge, paper mill sludge, cotton gin waste and other sources. These feedstocks can be utilized to produce a dried and pelletized fertilizer with high levels of organics, nitrates and phosphates (FIG. 10). The MEF process described herein can be utilized to convert the carbohydrates and cellulose into protein and provide reclaimed water to the host facility. The MEF process will reduce the mass of material to be transported as fertilizer by 80% to 95%, significantly reducing transportation costs. This fertilizer material can be manufactured on similar equipment to the HPAF train shown in FIG. 9, and delivered in a slow release pelletized form.

Example 4

Figure 11:
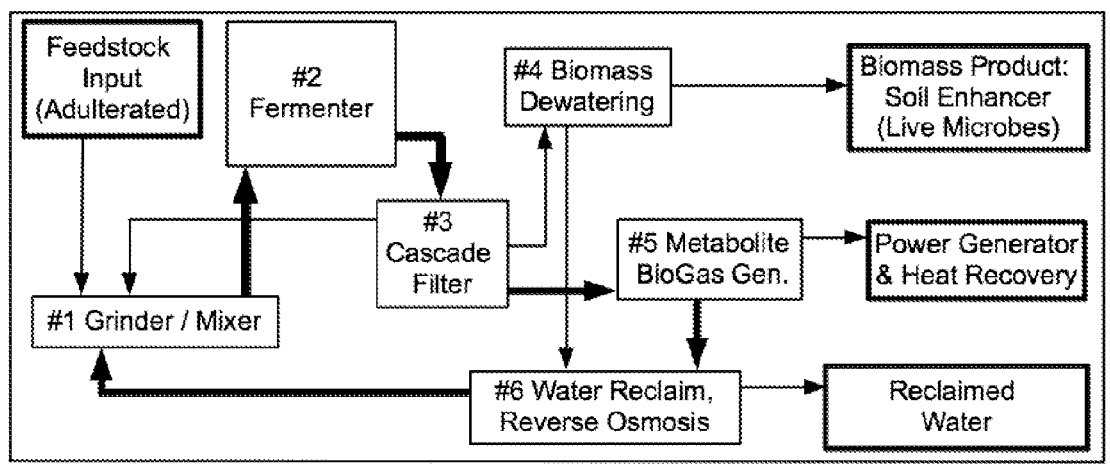
FIG. 11 is a flow diagram illustrating a Managed Ecosystem Fermentation (MEF) train for conversion of an adulterated organic waste feedstock to biomass that is partially dewatered to produce a soil enhancer product having living microbes to supplement the microbes that are found natively in soils.

A second product can be manufactured from the adulterated feedstock material using the same equipment train as the dry fertilizer shown in FIG. 10. By removing the biomass at a point in the process before it has been fully dewatered or denatured, the MEF can produce a liquid material with many living microbes to supplement the microbes that are found natively in soils (FIG. 11). Literature notes that many of the microbes found in rumen are also found in healthy soils, and often consumed by the ruminant while grazing. (Hungate, 1966) Observations have shown that liquid MEF biomass slurries are effective in stimulating plant growth. The method of extraction and delivery of these living microbes to the soil at a depth to minimize oxygen contact will require handling techniques that preserve the microbes in a live state.

The use of a liquid injection system on the farm allows the delivery of anaerobic microbes in a live condition, to re-inoculate soils that have had their endogenous microbes depleted. This equipment would be similar to that used today for liquid ammonia incorporation into agricultural soils.

Example 5

Processing of adulterated organics into biomass that is subsequently separated into separate species of protein materials using a cascade extraction devices as shown in FIG. 12.

The material supplied to this unit would be the wet biomass fraction typically sent to Unit #4, biomass dewatering, consisting of or comprising the cells plus the proteins, enzymes and amino acids not incorporated into the cells. This process may be installed at specific MEF sites or at a Central Facility serving may RCUs.

The process consists or comprises of a series of coarse filter elements into which have been incorporated functional sites with specific chemicals capable of bonding to specific proteins. There may be a large number of these filter elements in the train, where each element is functionalized to remove a separate protein species or protein family.

Figure 13:
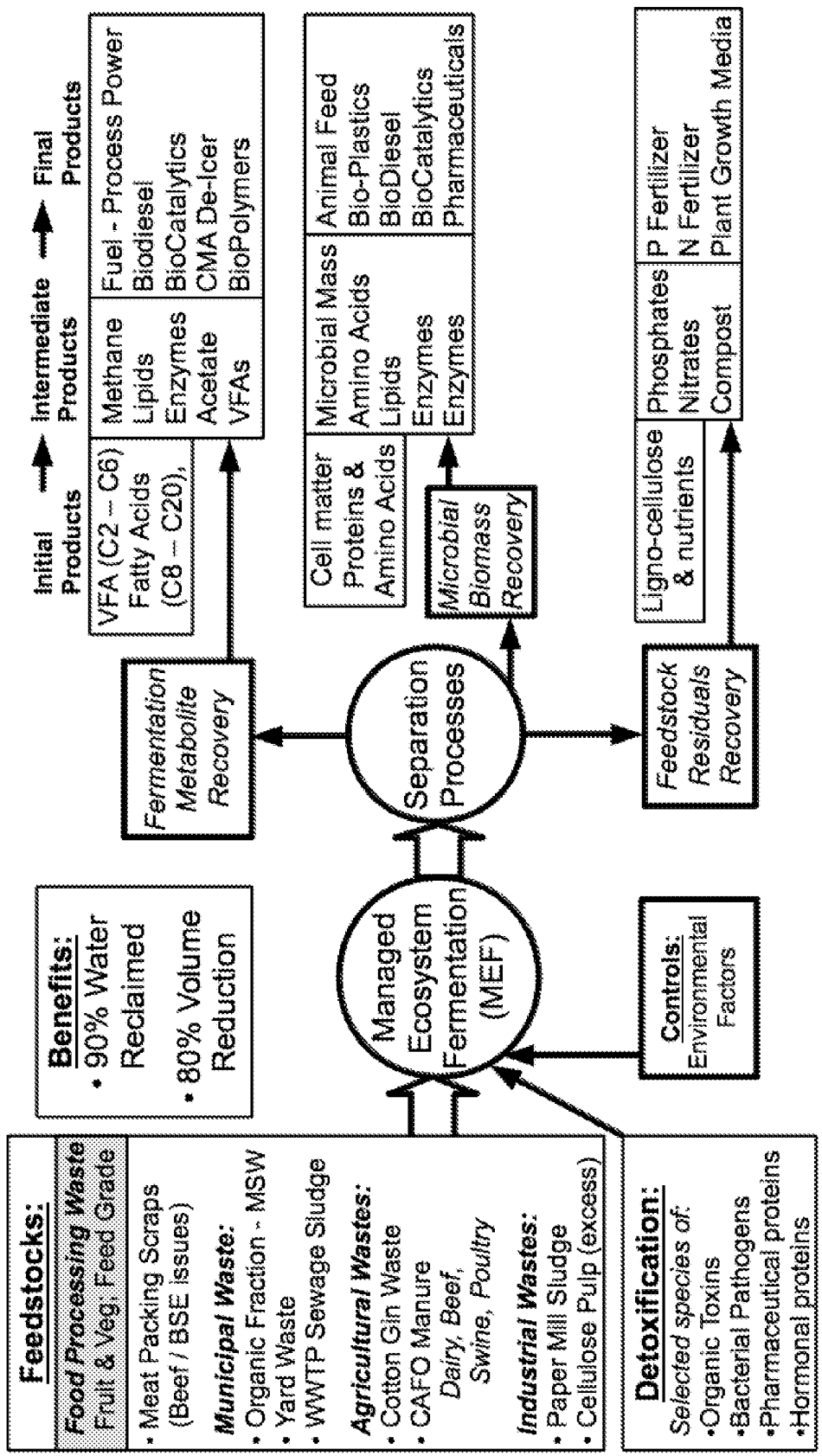
FIG. 13 is a flow diagram illustrating initial, intermediate, and final products that are generated by the Managed Ecosystem Fermentation (MEF) process described herein.
Figure 14:
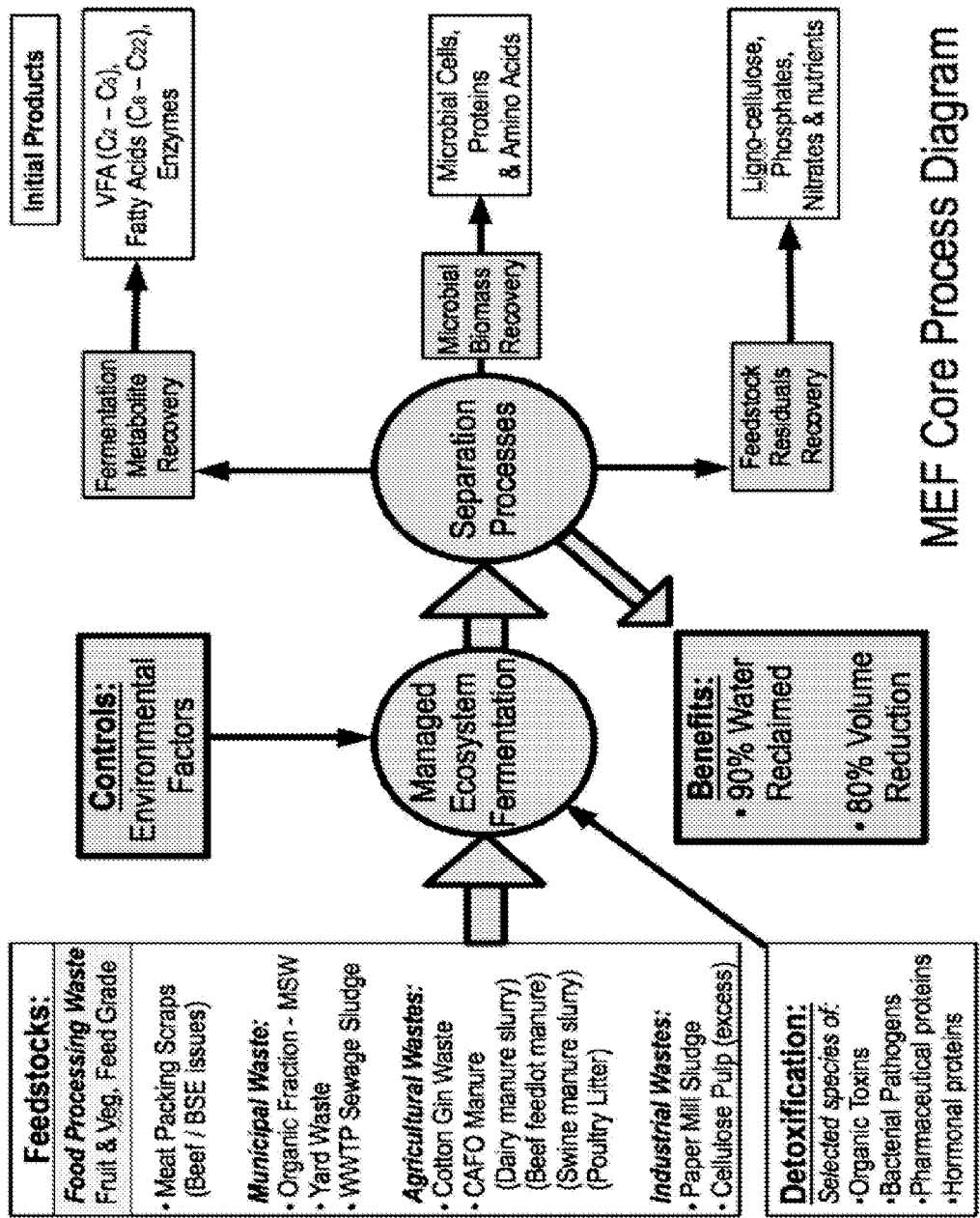
FIG. 14 is a flow diagram illustrating initial products that are generated by the Managed Ecosystem Fermentation (MEF) process described herein.

FIGS. 13 and 14 illustrate a flow diagram for one or more processes or methods according to one or more embodiments disclosed herein.

Example 6

Managed Ecosystem Fermentation (MEF) with Catering Waste as Feedstock

A MEF system was established by inoculating a feedstock of catering waste obtained from a local restaurant with rumen from a cannulated cow fed on a dairy diet for dry cows. This experiment demonstrates the ability of the rumen material to break down the catering waste feedstock into chemical products including volatile fatty acids (VFAs) and biomass for a culture period of over 100 days in a non-sterile system at 39° C. and close to atmospheric pressure. This experiment demonstrates the robustness and stability of the MEF for continuous production of chemical products and biomass.

The catering waste was obtained as a random sampling of scraps and collected in 5 gallon batches. The catering waste was ground in a blender to a maximum particle size of about $1/8^{th}$ inch in diameter and stored outside in a bucket with a non-sealing lid. No attempt was made to keep the catering waste feedstock sealed or sterile. The bovine rumen was from a cannulated cow fed on a dairy diet for dry cows and the rumen was obtained with little of the floating mat found inside the rumen organ. The rumen was stored as an active culture in an incubator at 39° C. for over 100 days with regular removal of material, dilution with artificial saliva (prepared as described on page 167 of Hungate, 1966, The Rumen and Its Microbes, Academic Press, New York), and fed on a diet of alfalfa and timothy hay compressed into pellets (sold commercially in pet stores as rabbit food).

The MEF was performed using the following materials and methods. The MEF was carried out in a 1 gallon (3.8 L) glass container having a metal top attached by screw threads molded into the glass. Three liters of fermentation liquid was placed in the glass container. The fermentation liquid was prepared by mixing (approx. 450 ml) of the ground catering waste with (approx. 1 liter) of artificial saliva prepared as described above. The fermentation liquid was placed in the fermentation container and inoculated with 500 ml of the bovine rumen. The top of the fermentation container was modified to provide a vent tube (¼ inch poly tubing) and a plastic film rupture disk, set to a relief pressure of approximately 20 inches of water. The other end of the vent tube was submerged into a jar of ammonia water to apply a back pressure on the jar of approximately 3 inches and also provide odor control by neutralizing the carboxylic acid vapors produced by the fermentation. The MEF was carried out in a constant temperature model 818 Dual Program Illuminated Incubator maintained at 39° C. (+/−0.5° C.) (PRECISION, THERMOFISHER).

The MEF was maintained on a 24 hour cycle using a daily process of removal of material and feeding. Material was extracted from the MEF container using a vacuum system as follows. An extraction nozzle was manufactured from ½ inch PVC pipe, with a vent hole for operator control of the extraction rate. The collection hose was manufactured from a nominal 1 inch flexible hose with molded rubber end fittings. The end fittings were modified to connect to the ½ inch PVC nozzles and ¾ inch PVC collection hose fitting on the extraction receiver tank. The extraction receiver tank was manufactured from a 5 gallon plastic bucket with resealable lid. The lid was modified with the addition of 1) a vacuum supply fitting (¼ inch threaded tube bulkhead fitting) for connecting the receiver tank to the vacuum pump assembly; 2) a collection hose fitting (¾ inch PVC pipe bulkhead fitting and hose slip connection) for connecting the collection hose; and 3) a vacuum regulator to limit the vacuum within the extraction vessel to a value that will not collapse the vessel, but still allow for sufficient suction to withdraw the MEF materials from the fermentation vessel. The vacuum pump was a standard dental vacuum pump, model 5711-130, manufactured by (SCHUCO, Williston Park, N.Y.). An on-off switch assembly has been provided for operator convenience.

Observation of the fermentation culture showed formation of a mat of material at the top of the culture, a liquid layer below the mat, and a layer of settled material at the bottom. The mat material contained both organic matter and lipid material. Each day, the pH of the MEF was measured and a sample of the liquid layer was removed for analysis by gas chromatography (GC). The pH was measured by inserting a pH probe (ORION Model 420A with a YSI-110-1 pH probe) through the mat at the top of the fermentation culture into the liquid layer below. The pH meter was calibrated using a pH 10.0 and pH 4.0 standard to provide a two point calibration and verified with a pH 7.0 standard. The sample for GC analysis was obtained by inserting a Pasteur pipette through the top mat of the culture and withdrawing 1.5 ml of the liquid below to a clean sample tube, acidifying with 2 drops of muriatic acid, and sealing the tube. Next, the MEF was maintained by removing about ⅓ of the total fermentation culture. About ⅓ of each of the mat, the liquid layer, and the settled bottom layer was separately removed. Removal of the liquid and bottom portions was performed by aspiration and removal of the top mat portion was performed by scooping with a spatula. About 500 ml of the catering waste feedstock and about 500 ml of the artificial saliva was then added back to the fermentation. The pH was again measured and recorded. The fermentation was sparged with $CO_2$ using a wand for about 10 seconds with the $CO_2$ regulator set at 5 psi. The lid of the fermentation container was reinstalled and the gas vent tube connecting the bulkhead fitting in the lid to the jar of ammonia water was attached.

The fermentation activity by the MEF was determined by GC analysis. The liquid layer that was sampled from the MEF on a daily basis as described above was tested by GC for the presence of chemicals including acetic acid, proprionic acid, isobutyric acid, butyric acid, isovaleric acid, valeric acid, lactic acid, hexanoic acid and glycerol. The samples from the liquid layer of the MEF were run on a HP 5890 Series II gas chromatograph with FID detector. The column was a RESTEK MXT-WAXDA 30 m×0.53 mm ID×1.00 um df, having maximum operating temperature of 240° C. The temperature program used was initial 40° C., hold for 2 min, ramp 10° C./min to 220° C., hold for 1 min at 220° C. The GC/FID was attached to a SRI Model 202 PEAKSIMPLE CHROMATOGRAPHY DATA SYSTEM controlled via a serial connection to a PC. The PC used PEAKSIMPLE 3.85 software (SRI INSTRUMENTS) for calibration and data processing. Peak position and area calibration was done using a 4 point method on standard solutions of known concentrations of methanol, acetone, ethanol, butanol, acetic acid, proprionic acid, isobutyric acid, butyric acid, isovaleric acid, valeric acid, hexanoic acid, and lactic acid. Experiments were analyzed using these calibrations. Data analysis was performed using OPEN OFFICE CALC and ORIGIN 7.5 software (ORIGINLAB, Inc.).

Figure 15:
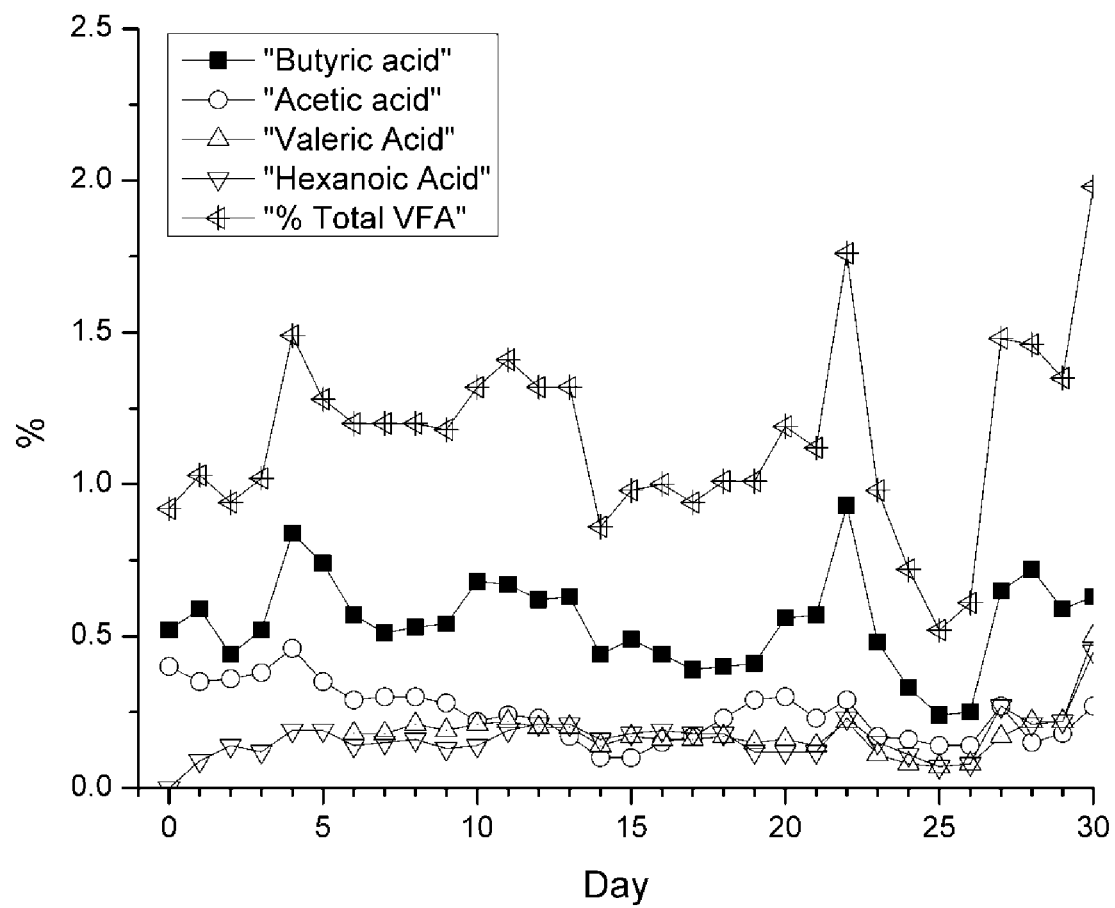
FIG. 15 is a graph showing the presence and daily fluctuation (over a 30 day period) in the liquid layer of an MEF of each of the VFAs: acetic acid, butyric acid, valeric acid, and hexanoic acid as a percent, as well as the percent total of these 4 VFAs.
Figure 16:
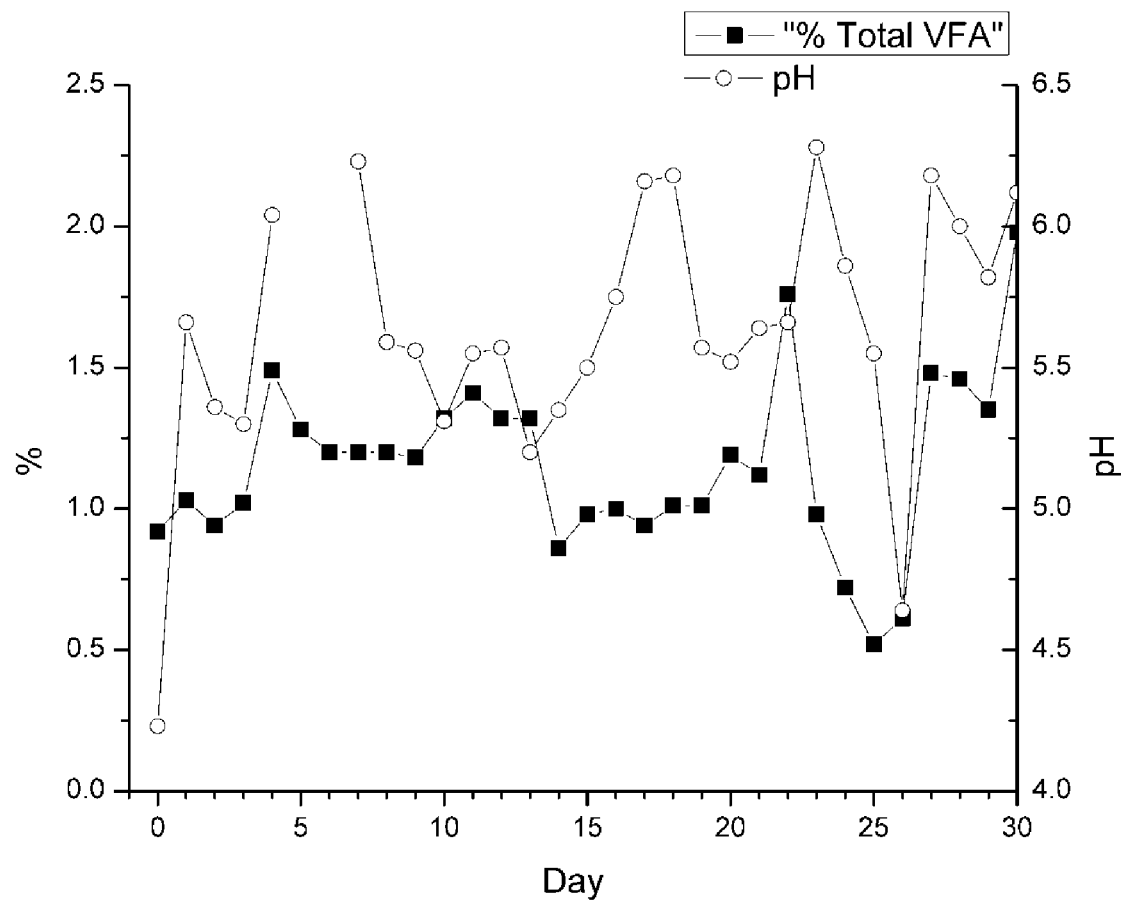
FIG. 16 is a graph showing the daily fluctuation in pH (circle symbols) and percent total of the 4 VFAs acetic acid, butyric acid, valeric acid, and hexanoic acid (square symbols) measured in the liquid layer of an MEF over a 30 day period.

FIG. 15 is a graph showing the presence and daily fluctuation (over a 30 day period) in the liquid layer of the MEF of each of the VFAs: acetic acid, butyric acid, valeric acid, and hexanoic acid as a percent, as well as the percent total of these 4 VFAs. FIG. 16 is a graph showing the daily fluctuation in pH (circle symbols) and percent total of the 4 VFAs acetic acid, butyric acid, valeric acid, and hexanoic (square symbols) measured in the liquid layer of the MEF over a 30 day period. These data demonstrate that the MEF was robust enough to withstand the wide swings in pH that occurred in the fermentation.

Example 7

Effect of pH on Chemical Production in Managed Ecosystem Fermentation (MEF)

Figure 17:
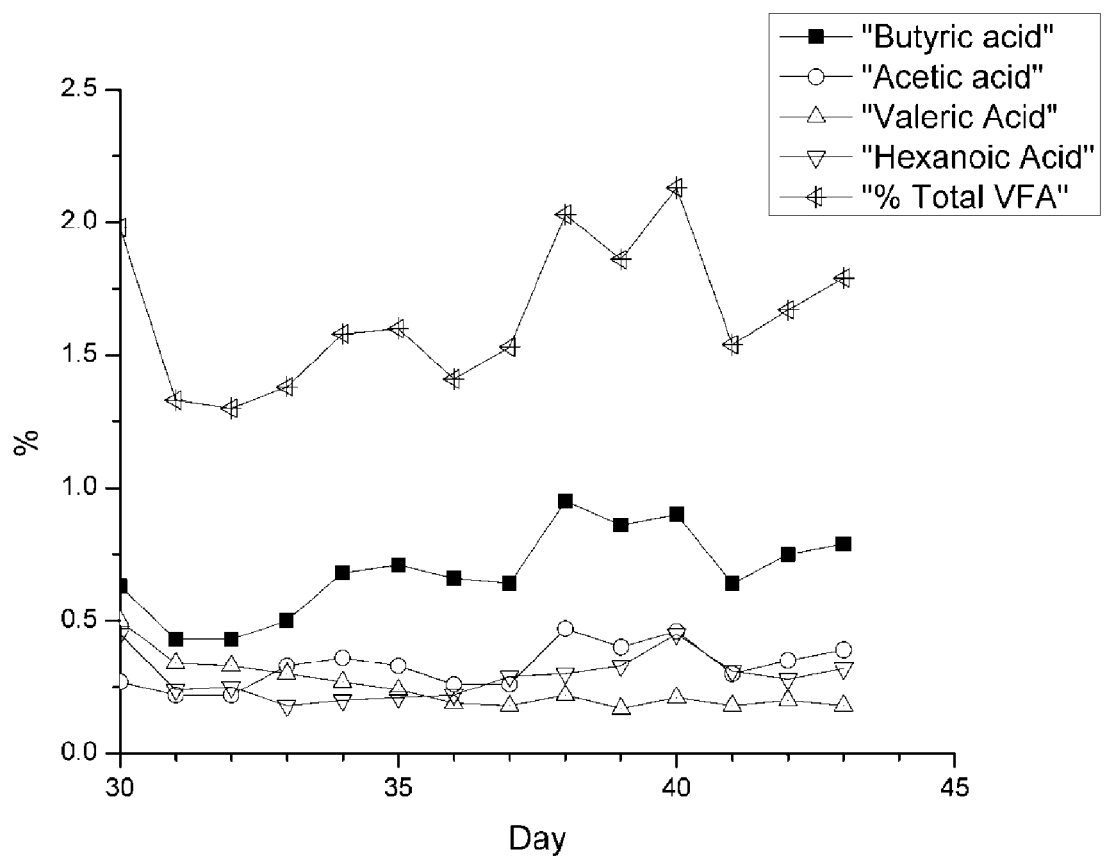
FIG. 17 is a graph showing the daily percent of each of the VFAs acetic acid, butyric acid, valeric acid, and hexanoic acid as well as the daily percent of the total of these 4 VFAs for an MEF with daily pH adjustment within a range 5.9-6.1.

This experiment was performed to determine the effect controlling the pH of the MEF on the production of chemicals including VFAs. The MEF was established and maintained as described above in Example 6. The change in daily procedure in this MEF was the adjustment of final pH after feeding by the addition of sodium bicarbonate to the MEF culture in an amount sufficient to raise the pH to a value of 5.9 to 6.1. FIG. 17 is a graph showing the daily percent of each of the VFAs acetic acid, butyric acid, valeric acid, and hexanoic acid as well as the daily percent of the total of these 4 VFAs for the MEF described above with daily pH adjustment within a range 5.9-6.1. The data in FIG. 17 show that adjusting the pH of the MEF each day to within a range of 5.9-6.1 resulted in an increased yield of VFAs.

Example 8

Biodiesel Waste as Feedstock for Managed Ecosystem Fermentation (MEF)

In this experiment an MEF was used to convert the process waste fluid from biodiesel manufacturing to chemicals including VFAs and biomass. Biodiesel waste is primarily glycerol and also includes carbohydrates, lipids, triglycerides, and a significant amount of methanol. The biodiesel waste for this experiment was obtained from a local biodiesel manufacturing plant for which it is a waste product and potentially a disposal problem. This material was a thick black liquid, with viscosity somewhat less than plain glycerol. The biodiesel waste material was stored in 1 gallon plastic jugs, with no environmental controls prior to addition to the MEF as a feedstock.

Figure 18:
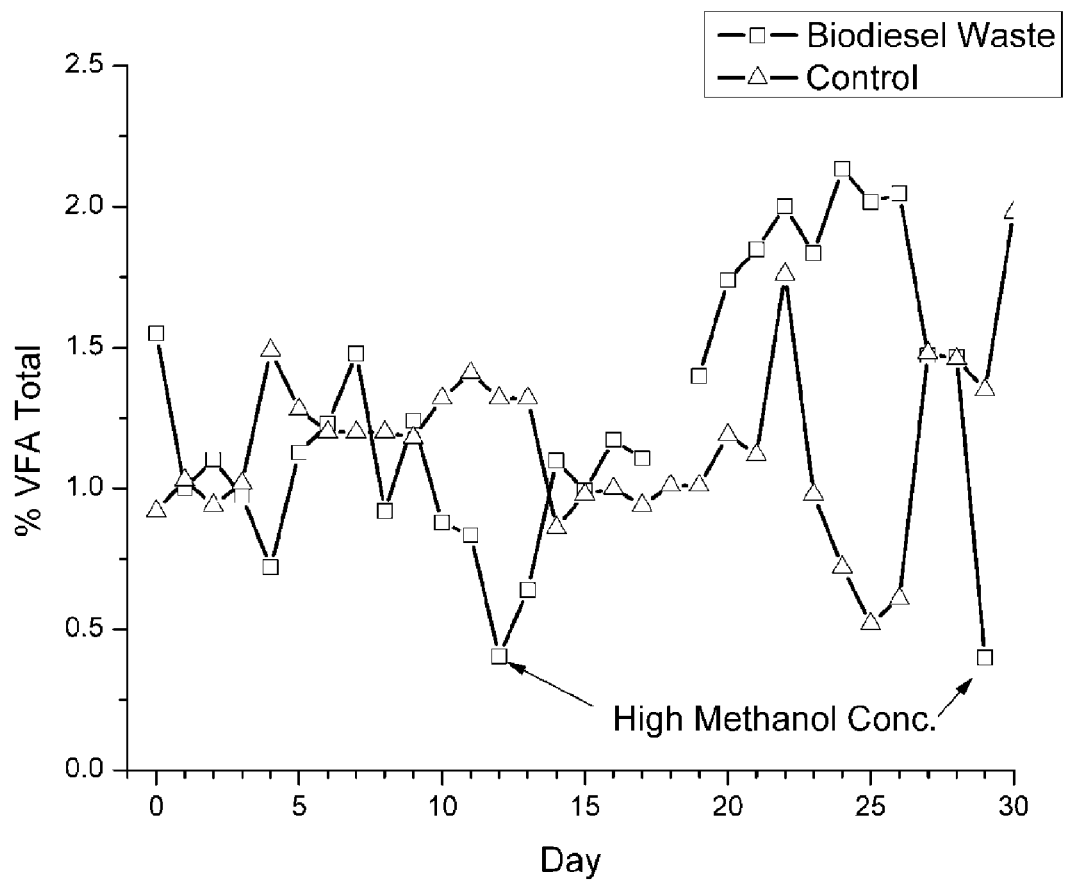
FIG. 18 is a graph showing total percent of the 4 VFAs acetic acid, butyric acid, valeric acid, and hexanoic acid in a control MEF (line with triangles) and an MEF with added biodiesel waste (line with squares).

It was first determined in a control experiment that the MEF according to Example 6 was capable of producing VFAs when reagent grade glycerol was added to the feedstock. The addition of reagent grade glycerol resulted in increased fermentation activity and gas generation, as well as increased VFA production with total consumption of the glycerol as shown in the GC runs (data not shown). For the experiment with added biodiesel waste, the MEF was established and maintained as described in Example 6 except that 100 ml of biodiesel waste was added each day to the MEF. The liquid phase of the MEF was sampled each day as described in Example 6 and analyzed by GC. The impact of the methanol in the biodiesel waste became apparent when the concentration of the methanol rose above about 2%. This high level of methanol appeared to harm the MEF and most VFA concentrations were greatly diminished for several days. FIG. 18 is a graph showing percent of total VFA in a control MEF and an MEF with added biodiesel waste, where the MEF with added biodiesel waste is represented by the line with squares and the control MEF is represented with triangles. As a result of the observed decrease in VFA production, the amount of biodiesel waste added to the MEF each day was reduced to 10 ml. After several days at this reduced level of biodiesel waste, the MEF recovered and the VFA concentrations were restored, but then the methanol levels again exceeded 2% and the VFA concentrations decreased (see FIG. 18 between days 12 and 30).

Example 9

Addition of *Clostridium Acetobutylicum* to Managed Ecosystem Fermentation (MEF)

In this experiment, additional bacteria were added to the MEF. In this case the bacterial strain, *Clostridium acetobutylicum*, a butyric acid producing bacteria, was added to the MEF to determine if total butyric acid production could be increased without negatively affecting the stability and robustness of the MEF. *C. acetobutylicum* was originally purchased from CAROLINA BIOLOGICAL SUPPLY, INC (Burlington, N.C.) and was cultured from spores on sterilized corn meal, according to the procedures developed by the Commercial Solvents Corporation (Butanol and Acetone from Corn, D H Killiffer, Industrial and Engineering Chemistry, vol 19, No 1, 1927). A MEF with added *C. acetobutylicum* was established by adding 500 ml of the culture of the *C. acetobutylicum* and was otherwise treated as the MEF in Example 6. A MEF established and maintained according to Example 6 was performed as a control experiment. The MEF cultures were maintained for a period of at least 30 days, and no significant changes in the stability or robustness of the MEF with the added *C. acetobutylicum* was observed. The percent production of the VFAs acetic acid, butyric acid, valeric acid, and hexanoic in the control MEF and the MEF with added *C. acetobutylicum* are shown in Table 3 below. The addition of *C. acetobutylicum* to the MEF resulted in more stable operation than the control fermentation in terms of pH and VFA production. The 45 day average amount of total acids produced per unit fermentation volume appeared to be about 8% higher with the addition of the *C. acetobutylicum* bacteria; however, there is a shift of about 15% from acetic acid to valeric and hexanoic acids, as measured by daily samples on the gas chromatograph.

Table 3. Comparison of Control MEF and MEF with added *Clostridium acetobutylicum* (45 day average)

TABLE 3

| Comparison of Control MEF and MEF with added *Clostridium acetobutylicum* (45 day average) | | | | | |
|---|---|---|---|---|---|
| | Acetic acid | Butyric Acid | Valeric acid | Hexanoic Acid | Total VFA |
| Control MEF | 0.27% | 0.59% | 0.20% | 0.20% | 1.29% |
| Plus *C. acetobutylicum* | 0.23% | 0.56% | 0.21% | 0.22% | 1.39% |
| Percent Difference | −15% | −5% | +5% | +10% | +8% |

Example 10

Variation of Feedstock in Managed Ecosystem Fermentation (MEF)

The experiments presented below are examples of modifying the feedstocks in MEF. It was observed that addition of ammonia to a MEF resulted in a visibly significant increase in the rate of fermentation. As a result, experiments are described using daily addition of ammonia and various feedstocks.

An experiment was performed where a MEF was established and maintained according to Example 6 (i.e. the feedstock was catering waste which is a high nitrogen feedstock) except that 20 ml of household ammonia, with a concentration of about 8% $NH_3$, was added to the MEF on a daily basis. This experiment was performed to determine if addition of a nitrogen source to a MEF that was already being cultured on a high nitrogen feedstock would further increase VFA production. The data in Table 4 below show the effect on the percent of each of the VFAs acetic acid, butyric acid, valeric acid and hexanoic acid produced for this MEF receiving addition of ammonia relative to a control MEF established and maintained according to Example 6. The data in Table 4 demonstrate that addition of ammonia to the MEF resulted in a significant increase in overall acid production, with the major gains in acetic and hexanoic acids.

Table 4. Comparison of Control MEF and MEF with Daily Addition of Ammonia

TABLE 4

| Comparision of Control MEF and MEF with Daily Addition of Ammonia | | | | | |
|---|---|---|---|---|---|
| | Acetic acid | Butyric Acid | Valeric acid | Hexanoic Acid | Total VFA |
| Control MEF | 0.27% | 0.59% | 0.20% | 0.20% | 1.29% |
| Plus Daily Ammonia | 0.41% | 0.63% | 0.20% | 0.28% | 1.63% |
| Percent Difference | +52% | +7% | 0.00% | +40% | +26% |

In the following experiment an MEF is established and maintained on a combination of the high nitrogen feedstock catering waste and the high carbon/low nitrogen feedstock wood pulp. In addition, ammonia is added to the MEF on a daily basis. More specifically, the MEF is established and maintained as described in Example 6 except that the feedstock is a combination of catering waste and wood pulp at a ratio of about 90:10 and, in addition, the MEF is supplemented with 20 ml of household ammonia on a daily basis as described in this Example above.

In the following experiment, a MEF is established and maintained except that a combination feedstock comprising catering waste and low nitrogen shredded newspaper is utilized as the feedstock for the MEF. More specifically, a MEF is established and maintained as described in Example 6 except that the feedstock is a combination of catering waste and shredded newspaper at a ratio of about 90:10 and, in addition, the MEF is supplemented with 20 ml of household ammonia on a daily basis as described in this Example above.

In the following experiment, a MEF is established using a combination feedstock where each of the feedstock components lacks either sufficient nitrogen or sufficient carbon on its own to maintain the MEF. Specifically, in this experiment a MEF is established and maintained as described in Example 6 except that the feedstock is a mixture of about 10% low carbon/high nitrogen sewage sludge and about 90% high carbon/low nitrogen municipal waste.

Example 11

Rumen Variation in Managed Ecosystem Fermentation (MEF)

The following experiments describe MEFs established using rumen from different animals or combinations of different rumens.

In this experiment, a MEF was established and maintained as described in Example 6 except that the bovine rumen was replaced with sheep rumen. For this experiment, initially 60 ml of sheep rumen was obtained from a veterinarian and cultured over several days as described above for the bovine rumen in Example 6 to a volume of greater than a gallon. At that point, an MEF was established and maintained as described above in Example 6. The use of sheep rumen proved reliable, but with lower overall acid yields. The one increase was measured in acetic acid production.

Table 5. Comparison of Control MEF and MEF of Sheep Rumen

TABLE 5

Comparison of Control MEF and MEF of Sheep Rumen

|  | Acetic acid | Butyric Acid | Valeric acid | Hexanoic acid | Total VFA |
| --- | --- | --- | --- | --- | --- |
| Control MEF | 0.27% | 0.59% | 0.20% | 0.20% | 1.29% |
| MEF of Sheep Rumen | 0.41% | 0.30% | 0.13% | 0.10% | 1.05% |
| Percent Difference | +52% | −49% | −35.00% | −50% | −20% |

In this experiment, a combination of bovine rumen and sheep rumen was used in a MEF. For this experiment, a new MEF was established and maintained as described in Example 6 except that 750 ml each of bovine rumen and the sheep rumen grown in an MEF was used with 1 liter of artificial saliva to establish the new MEF. Table 7 below shows a comparison of VFA production by the control MEF and the MEF established with equal amounts of bovine and sheep rumen. The inclusion of the sheep rumen in the MEF resulted in a decrease in the average total VFAs produced by the fermentation. While the acetic acid increased, the other significant acid production levels decreased on the catering waste feedstock.

Table 6. Comparison of Control MEF and MEF with Bovine/Sheep Rumen Blend

TABLE 6

Comparison of Control MEF and MEF with Bovine/Sheep Rumen Blend

|  | Acetic Acid | Butyric Acid | Valerie Acid | Hexanoic Acid | Total VFA |
| --- | --- | --- | --- | --- | --- |
| Control MEF | 0.27% | 0.59% | 0.20% | 0.20% | 1.29% |
| Bovine Plus Sheep | 0.41% | 0.30% | 0.12% | 0.12% | 1.03% |
| Percent Difference | 52% | −49% | −40% | −40% | −20% |

In this experiment, a MEF is established and maintained in which the rumen is supplemented with ground earth worms to provide earth worm microbes to the MEF based on the use of vermiculture for composting. Specifically, a MEF is established and maintained according to Example 6 except that 1 liter of freshly ground earth worms is included with the addition of the rumen at the establishment of the MEF.

In this experiment, a MEF is established and maintained in which the rumen is supplemented with ground termites to provide termite microbes to the MEF based on the use of cellulase enzymes from termites to break down cellulose (Tokuda & Watanabe, 2007). Specifically, a MEF is established and maintained according to Example 6 except that 1 liter of freshly ground termites is included with the addition of the rumen at the establishment of the MEF.

The following references are hereby incorporated in their entirety:

Adenije, A A, Jimoh, A, "Effects of Replacing Maize with Enzyme Supplemented Bovine Rumen Content in the Diets of Pullet Chicks" *International Journal of Poultry Science* 6 (11): 814-817, 2007.

Bata, Lasztity, "Detoxification of mycotoxin-contaminated food and feed by microorganisms," *Trends in Food Science & Technology* 10, 223-228, 1999.

Brooker, "Tannins in Livestock and Human Nutrition," ACIAR Proceedings No. 92, 2005 http://www.smallstock.info/reference/ACIAR/Tannins/PR92—Part1.pdf] (compilation of related papers).

Brooker, "Rumen microorganisms as providers of high quality protein," Livestock Research for Rural Development, Vol. 6, No. 3, March 1995. http://www.lrrd.org/lrrd6/3/1.htm Calt, E., "Island Financial Resource Impacts from Managed Ecosystem Fermentations for the Treatment of Organic Waste Streams," IEA Conference," 2011.

Feitshans, "Federal Regulation of Industrial Biotechnology in the United States, IEA Conference," 2011.

Gregg, "Biological world-first for Rumen Biotech Group," Synergy, Vol. 2, No. 2, Winter, 1998, http://wwwcomm.murdoch.edu.au/synergy/9802/rumen.html.

Hungate, R E, "The Rumen and Its Microbes." Academic Press, New York, 1966.

Hungate, R E, "The Rumen Microbial Ecosystem," *Annual Review of Ecology and Systematics*, Vol. 6, pp. 39-66, 1975. Stable URL: http://www.jstor.org/stable/2096824

Sauvant, "Modeling Rumen Carbon Partitioning", Bovidig database, 2009, https://colloque2.inra.fr/ . . . /content/ . . . /Sauvant_ModRu__7Modnutpres.pdf.

Tokuda & Watanabe, *Biol. Lett.* 3: 336-339, 2007.

Weimer, "Manipulating Ruminal Fermentation: A Microbial Ecological Perspective," *J. Anim. Sci.* 76:3114-3122, 1998.

What is claimed is:

1. A system for generating resources from organic feedstock(s), the system comprising:
    a grinder/mixer configured to receive an organic feedstock and an isolated rumen; and
    a mechanically controlled fermenter comprising the isolated rumen, wherein the mechanically controlled fermenter is configured to ferment the organic feedstock in a continuous managed ecosystem fermentation (MEF) to generate a resource.

2. The system of claim 1, wherein the organic feedstock comprises one of catering waste, biodiesel waste, agricultural waste, food processing plant waste, wood pulp, shredded paper, paper mill sludge, cotton gin waste, sewage sludge, slaughter house waste, organic fraction of municipal solid waste (OFMSW), algae, and combinations thereof.

3. The system of claim 1, wherein the organic feedstock comprises catering waste.

4. The system of claim 1, wherein the resource comprises lipids, volatile fatty acids, long chain fatty acids, biomass, high protein animal feed, fertilizer, phosphate fertilizer, nitrogen fertilizer, proteins, amino acids, enzymes, ethanol, butanol, biogas, or water, and combinations thereof.

5. The system of claim 4, wherein the volatile fatty acids comprise acetic acid, proprionic acid, isobutyric acid, butyric acid, isovaleric acid, valeric acid, lactic acid or hexanoic acid, and combinations thereof.

6. The system of claim 4, wherein the amino acids comprise lysine.

7. The system of claim 4, wherein the enzymes comprise cellulase, alpha-amylase, histidase, lysozyme or penicillin acylase, and combinations thereof.

8. The system of claim 4, wherein the biogas comprises methane, hydrogen or carbon dioxide, and combinations thereof.

9. The system of claim 1, wherein the isolated rumen comprises a bovine rumen, a sheep rumen, a goat rumen, a deer rumen, or a bison rumen, and combinations thereof.

10. The system of claim 1, wherein the isolated rumen comprises bovine rumen.

11. The system of claim 1, wherein the fermenter is further configured to receive a microorganism comprising a bacteria, a yeast, a fungi, a protozoa, earth worm microbes, termite microbes, or cecum microbes, and combinations thereof.

12. The system of claim 11, wherein the bacteria comprises a butyric acid producing bacteria, a cellulosic bacteria or a *Clostridium acetobutylicium* bacteria, and combinations thereof.

13. The system of claim 11, wherein the yeast comprises an industrial yeast or a brewer's yeast, and combinations thereof.

14. The system of claim 11, wherein the fungi comprises a *Trichoderma reesei*.

15. The system of claim 11, wherein the cecum microbes comprise rabbit cecum microbes or horse cecum microbes, and combinations thereof.

16. The system of claim 1, wherein the fermenter is further configured to receive a butyric acid producing bacteria.

17. The system of claim 1, wherein the resource comprises chemicals and wherein the system is configured to remove from the fermenter a portion of the chemicals that are acidic to maintain the pH in a range between about pH 4 to about pH 9.

18. The system of claim 1, wherein the resource comprises chemicals, and wherein the fermenter is configured to fractionate the chemicals.

19. The system of claim 18, further comprising a chemical separation unit configured to separate the fractionated chemicals.

20. The system of claim 19, wherein chemicals fractionated by the chemical separation unit comprise volatile fatty acids or long chain fatty acids, and combinations thereof, and wherein the chemical separation unit comprises an ion exchange technology.

21. The system of claim 20, wherein the volatile fatty acids comprise acetic acid, proprionic acid, isobutyric acid, butyric acid, isovaleric acid, valeric acid, lactic acid or hexanoic acid, and combinations thereof.

22. The system of claim 1, wherein the resource comprises chemicals, the system further comprising:
a biogas generator configured as an additional fermenter to receive the isolated rumen and at least a portion of the chemicals to ferment the chemicals and the isolated rumen in the biogas generator to generate biogas.

23. The system of claim 1, wherein the resource comprises biomass, wherein the fermenter is configured to fractionate the biomass through particulate separation, the system further comprising:
a dewatering unit configured to dewater the fractionated biomass.

24. The system of claim 23, wherein the dewatered biomass is a soil enhancer having live microbes.

25. The system of claim 23, further comprising a drying unit to dry dewatered biomass.

26. The system of claim 25, wherein the organic feedstock is a feed grade feedstock and wherein the biomass is a dewatered and dried high protein animal feed (HPAF).

27. The system of claim 25, wherein the biomass is a dewatered and dried dry fertilizer.

28. The system of claim 1, wherein the resource comprises chemicals, biomass, lipids, and biogas, wherein the fermenter is further configured to fractionate the resource, and the system further comprises:
a chemical separation unit configured to fractionate the chemicals to generate a chemical product; and
a biomass separation unit configured to fractionate the biomass to generate a biomass product.

29. The system of claim 1, further comprising a power generation and heat recovery unit configured to generate power and heat, wherein one of the generated power and heat are utilized in the system.

30. The system of claim 1, wherein the resource comprises chemicals, biomass, and biogas, wherein the fermenter is further configured to fractionate the resource, and the system further comprises:
a chemical separation unit configured to fractionate the chemicals to generate a chemical product; and
a biomass separation unit configured to fractionate the biomass to generate a biomass product.

31. The system of claim 30, wherein the resource comprises lipids and the fermenter configured to fractionate the resource lipids.

32. The system of claim 1, wherein the continuous MEF is capable of being maintained for at least 30 days.

* * * * *